(12) United States Patent
Zhang et al.

(10) Patent No.: US 10,555,684 B2
(45) Date of Patent: Feb. 11, 2020

(54) SUPRAVENTRICULAR TACHYARRHYTHMIA DISCRIMINATION

(71) Applicant: Medtronic, Inc., Minneapolis, MN (US)

(72) Inventors: Xusheng Zhang, Shoreview, MN (US); Jian Cao, Shoreview, MN (US); Yuanzhen Liu, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 171 days.

(21) Appl. No.: 15/496,309

(22) Filed: Apr. 25, 2017

(65) Prior Publication Data

US 2018/0303368 A1 Oct. 25, 2018

(51) Int. Cl.
*A61B 5/0464* (2006.01)
*A61B 5/0456* (2006.01)
(Continued)

(52) U.S. Cl.
CPC ........ *A61B 5/0464* (2013.01); *A61B 5/04012* (2013.01); *A61B 5/0456* (2013.01); *A61N 1/08* (2013.01); *A61N 1/36585* (2013.01); *A61N 1/3925* (2013.01); *A61N 1/3956* (2013.01); *A61N 1/3987* (2013.01); *A61N 1/025* (2013.01);
(Continued)

(58) Field of Classification Search
CPC . A61B 5/0464; A61B 5/04012; A61B 5/0456; A61N 1/08; A61N 1/36585; A61N 1/3925; A61N 1/3956; A61N 1/3987; A61N 1/025; A61N 1/0587; A61N 1/3704; A61N 1/0563
See application file for complete search history.

(56) References Cited

U.S. PATENT DOCUMENTS 5,240,009 A 8/1993 Williams
5,354,316 A 10/1994 Keimel
(Continued)

FOREIGN PATENT DOCUMENTS

EP 0813888 A1 12/1997
WO 2005065772 A1 7/2005
(Continued)

OTHER PUBLICATIONS

Schuckers, "Arrhythmia Analysis, Automated", Encyclopedia of Medical Devices and Instrumentation, Second Edition, Apr. 14, 2006, 16 pages.
(Continued)

*Primary Examiner* — Lindsey G Wehrheim

(57) ABSTRACT

An implantable cardioverter defibrillator (ICD) performs a method that includes determining whether first criteria for detecting a ventricular tachyarrhythmia are met by a cardiac electrical signal. The ICD determines features from cardiac signal segment of a group of cardiac signal segments and determines whether a first portion of the features satisfy monomorphic waveform criteria and determines whether a second portion of the features satisfy supraventricular beat criteria. The ICD determines whether second criteria for detecting the ventricular tachyarrhythmia are met and withholds detecting of the ventricular tachyarrhythmia in response to the monomorphic waveform criteria and the supraventricular beat criteria being met.

27 Claims, 15 Drawing Sheets

(51) Int. Cl.
*A61N 1/39* (2006.01)
*A61B 5/04* (2006.01)
*A61N 1/08* (2006.01)
*A61N 1/365* (2006.01)
*A61N 1/05* (2006.01)
*A61N 1/02* (2006.01)
*A61N 1/37* (2006.01)

(52) U.S. Cl.
CPC .......... *A61N 1/0563* (2013.01); *A61N 1/0587* (2013.01); *A61N 1/3704* (2013.01)

(56) References Cited

U.S. PATENT DOCUMENTS

| | | | |
|---|---|---|---|
| 5,545,186 | A | 8/1996 | Olson et al. |
| 5,846,263 | A * | 12/1998 | Peterson .............. A61N 1/3622 607/14 |
| 5,893,882 | A | 4/1999 | Peterson et al. |
| 6,212,428 | B1 | 4/2001 | Hsu et al. |
| 6,393,316 | B1 | 5/2002 | Gillberg et al. |
| 6,810,283 | B2 | 10/2004 | Suribhotla et al. |
| 7,031,771 | B2 | 4/2006 | Brown et al. |
| 7,062,315 | B2 | 6/2006 | Koyrakh et al. |
| 7,076,289 | B2 | 7/2006 | Sarkar et al. |
| 7,706,869 | B2 | 4/2010 | Cao et al. |
| 7,751,873 | B2 | 7/2010 | de Voir |
| 7,761,150 | B2 | 7/2010 | Ghanem et al. |
| 8,160,684 | B2 | 4/2012 | Ghanem et al. |
| 8,165,675 | B2 | 4/2012 | Wang et al. |
| 8,271,081 | B2 | 9/2012 | Hauck et al. |
| 8,332,022 | B2 | 12/2012 | Brown et al. |
| 8,428,697 | B2 | 4/2013 | Zhang et al. |
| 8,437,842 | B2 | 5/2013 | Zhang et al. |
| 8,543,198 | B2 | 9/2013 | Zhang et al. |
| 8,768,459 | B2 | 7/2014 | Ghosh et al. |
| 8,825,145 | B1 | 9/2014 | Zhang |
| 8,983,585 | B2 | 3/2015 | Zhang et al. |
| 8,983,586 | B2 | 3/2015 | Zhang |
| 9,526,908 | B2 | 12/2016 | Zhang et al. |
| 2010/0036447 | A1 | 2/2010 | Zhang et al. |
| 2014/0323894 | A1 | 10/2014 | Zhang et al. |
| 2015/0306375 | A1 | 10/2015 | Marshall et al. |
| 2015/0306410 | A1 | 10/2015 | Marshall et al. |
| 2016/0022166 | A1 | 1/2016 | Stadler et al. |
| 2016/0022999 | A1 | 1/2016 | Zhang et al. |
| 2016/0158567 | A1 | 6/2016 | Marshall et al. |
| 2017/0027463 | A1 | 2/2017 | Du et al. |

FOREIGN PATENT DOCUMENTS

| | | |
|---|---|---|
| WO | 2007024920 A2 | 3/2007 |
| WO | 2017027272 A1 | 2/2017 |

OTHER PUBLICATIONS (PCT/US2018/027708) PCT Notification of Transmittal of the International Search Report and the Written Opinion of the International Searching Authority, dated Aug. 13, 2018, 16 pages.

Zhang, et al., "System and Method for Sensing and Detection in an Extra-Cardiovascular Implantable Cardioverter Defibrillator", U.S. Appl. No. 15/140,802, filed Apr. 27, 2016, 77 pages.

Cao et al., "Multi-Threshold Sensing of Cardiac Electrical Signals in an Extracardiovascular Implantable Cardioverter Defibrillator", U.S. Appl. No. 15/142,171, filed Apr. 29, 2016, 71 pages.

Greenhut et al., "Cardiac Electrical Signal Noise Detection for Tachyarrhythmia Episode Rejection", U.S. Appl. No. 62/367,170, filed Jul. 27, 2016, 94 pages.

Zhang et al., "Cardiac Electrical Signal Gross Morphology-Based Noise Detection for Rejection of Ventricular Tachyarrhythmia Detection", U.S. Appl. No. 62/367,166, filed Jul. 27, 2016, 93 pages.

Cao et al., "Cardiac Electrical Signal Morphology and Pattern-Based T-Wave Oversensing Rejection", U.S. Appl. No. 62/367,221, filed Jul. 27, 2016, 92 pages.

\* cited by examiner

SUPRAVENTRICULAR TACHYARRHYTHMIA DISCRIMINATION

TECHNICAL FIELD

The disclosure relates generally to an implantable medical device system and method for discriminating supraventricular tachyarrhythmia from ventricular tachyarrhythmia.

BACKGROUND

Medical devices, such as cardiac pacemakers and implantable cardioverter defibrillators (ICDs), provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals.

Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation. The ICD may sense the cardiac electrical signals in a heart chamber and deliver electrical stimulation therapies to the heart chamber using electrodes carried by transvenous medical electrical leads. Cardiac signals sensed within the heart generally have a high signal strength and quality for reliably sensing cardiac electrical events, such as R-waves. In other examples, a non-transvenous lead may be coupled to the ICD, in which case cardiac signal sensing presents new challenges in accurately sensing cardiac electrical events and properly detecting and discriminating between different types of cardiac arrhythmias.

Proper detection and discrimination of different tachyarrhythmias is important in automatically selecting and delivering an effective electrical stimulation therapy by an implantable medical device system and avoiding unnecessary therapies. For example, a supraventricular tachyarrhythmia originates in the upper, atrial heart chambers and is conducted to the lower, ventricular heart chambers. A supraventricular tachyarrhythmia (SVT) is generally not successfully terminated by delivering electrical stimulation therapy to the ventricles because the heart rhythm is arising from the upper heart chambers. A ventricular tachyarrhythmia that originates in the lower, ventricular heart chambers, on the other hand, generally can be successfully treated by delivering electrical stimulation therapies to the ventricles to terminate the abnormal ventricular rhythm. Accordingly, discrimination of supraventricular tachyarrhythmia that originates in the upper heart chambers from ventricular tachyarrhythmia that originates in the lower heart chambers allows for appropriate therapy selection and delivery while avoiding unnecessary or potentially ineffective electrical stimulation therapy from being delivered to the patient's heart.

SUMMARY

In general, the disclosure is directed to techniques for discriminating SVT from ventricular tachyarrhythmias, e.g., ventricular tachycardia (VT) and ventricular fibrillation (VF), and withholding VT and VF detection and therapies when SVT is detected. In some examples, an ICD system operating according to the techniques disclosed herein may determine features of cardiac signal segments corresponding to sensed R-waves that occur at a tachyarrhythmia rate and have a morphology indicative of ventricular tachycardia. A first group of the determined cardiac signal segment features may be compared to monomorphic rhythm criteria and a second group of the determined features may be compared to SVT beat criteria. If the monomorphic rhythm criteria and the SVT beat criteria are both satisfied, the rhythm may be identified as a supraventricular rhythm. Ventricular tachyarrhythmia detection and therapy are delayed or withheld in response to detecting the supraventricular rhythm.

In one example, the disclosure provides an ICD including a therapy delivery circuit, a sensing circuit and a control circuit coupled to the sensing circuit and the therapy delivery circuit. The therapy delivery circuit is configured to generate an electrical stimulation therapy for delivery to a patient's heart. The sensing circuit is configured to receive a cardiac electrical signal via a sensing electrode vector. The control circuit is configured to determine whether first criteria for detecting a ventricular tachyarrhythmia are met by the cardiac electrical signal and determine features of each one of a group of cardiac signal segments of the cardiac electrical signal. In response to the first criteria being met, the control circuit determines whether a first portion of the features determined from each one of the cardiac signal segments satisfy monomorphic waveform criteria and determine whether a second portion of the features determined from each one of the cardiac signal segments satisfy supraventricular beat criteria. The control circuit determines whether second criteria for detecting the ventricular tachyarrhythmia are met and withholds detecting of the ventricular tachyarrhythmia in response to both the monomorphic waveform criteria being satisfied and the supraventricular beat criteria being satisfied. The control circuit detects the ventricular tachyarrhythmia and controls the therapy delivery circuit to deliver the electrical stimulation therapy in response to the first criteria and the second criteria being met and at least one of the monomorphic waveform criteria not being satisfied and/or the supraventricular beat criteria not being satisfied.

In another example, the disclosure provides a method including receiving by a sensing circuit a cardiac electrical signal via a sensing electrode vector, determining by a control circuit whether first criteria for detecting a ventricular tachyarrhythmia are met by the cardiac electrical signal, determining features of each one of a group of cardiac signal segments of the cardiac electrical signal and, in response to the first criteria being met, determining whether a first portion of the features determined from each one of the cardiac signal segments satisfy monomorphic waveform criteria and whether a second portion of the features determined from each one of the cardiac signal segments satisfy supraventricular beat criteria. The method further includes determining whether second criteria for detecting the ventricular tachyarrhythmia are met, determining whether both the first portion of the plurality of features satisfy the monomorphic waveform criteria and the second portion of the plurality of features satisfy the supraventricular beat criteria, and withholding detecting of the ventricular tachyarrhythmia in response both the first portion of the plurality of features satisfying the monomorphic waveform criteria and the second portion of the plurality of features satisfying the supraventricular beat criteria. The method includes detecting the ventricular tachyarrhythmia and controlling the therapy delivery circuit to deliver the electrical stimulation therapy in response to the first criteria and the second criteria being met and at least one of the first portion of the plurality of features not satisfying the monomorphic waveform criteria and/or the second portion of the plurality of features not satisfying the supraventricular beat criteria.

In another example, the disclosure provides a non-transitory, computer-readable storage medium storing a set of instructions which, when executed by a control circuit of an ICD, cause the ICD to receive by a sensing circuit a cardiac electrical signal via a sensing electrode vector; determine whether first criteria for detecting a ventricular tachyarrhythmia are met by the cardiac electrical signal;

determine features of each one of a group of cardiac signal segments of the cardiac electrical signal; in response to the first criteria being met, determine whether a first portion of the features determined from each one of the cardiac signal segments satisfy monomorphic waveform criteria; determine whether a second portion of the features determined from each one of the cardiac signal segments satisfy supraventricular beat criteria; determine whether second criteria for detecting the ventricular tachyarrhythmia are met; withhold detecting of the ventricular tachyarrhythmia in response to both the monomorphic waveform criteria being satisfied and the supraventricular beat criteria being satisfied; and detect the ventricular tachyarrhythmia and deliver an electrical stimulation therapy by a therapy delivery circuit in response to the first criteria and the second criteria being met and at least one of the monomorphic waveform criteria not being satisfied or the supraventricular beat criteria not being satisfied.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for discriminating SVT from VT and VF by a cardiac medical device or system and withholding detection of a ventricular tachyarrhythmia in response to detecting SVT. Criteria for detecting ventricular tachyarrhythmia, such as heart rate-based criteria, may become satisfied in the presence of SVT. As such, heart rate alone may be insufficient for reliably discriminating between SVT and VT/VF. Techniques for detecting SVT as described herein allow a tachyarrhythmia detection to be withheld when evidence of SVT is identified.

In some examples, the cardiac medical device system may be an extra-cardiovascular ICD system. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein for detecting SVT and withholding a VT/VF detection may be applied to a cardiac electrical signal acquired using extra-cardiovascular electrodes.

These techniques are presented herein in conjunction with an ICD and implantable medical lead carrying extra-cardiovascular electrodes, but aspects disclosed herein may be utilized in conjunction with other cardiac medical devices or systems. For example, the techniques for detecting SVT as described in conjunction with the accompanying drawings may be implemented in any implantable or external medical device enabled for sensing cardiac electrical signals, including implantable pacemakers, ICDs or cardiac monitors coupled to transvenous, pericardial or epicardial leads carrying sensing and therapy delivery electrodes; leadless pacemakers, ICDs or cardiac monitors having housing-based sensing electrodes; and external or wearable pacemakers, defibrillators, or cardiac monitors coupled to external, surface or skin electrodes.

Figure 1A:
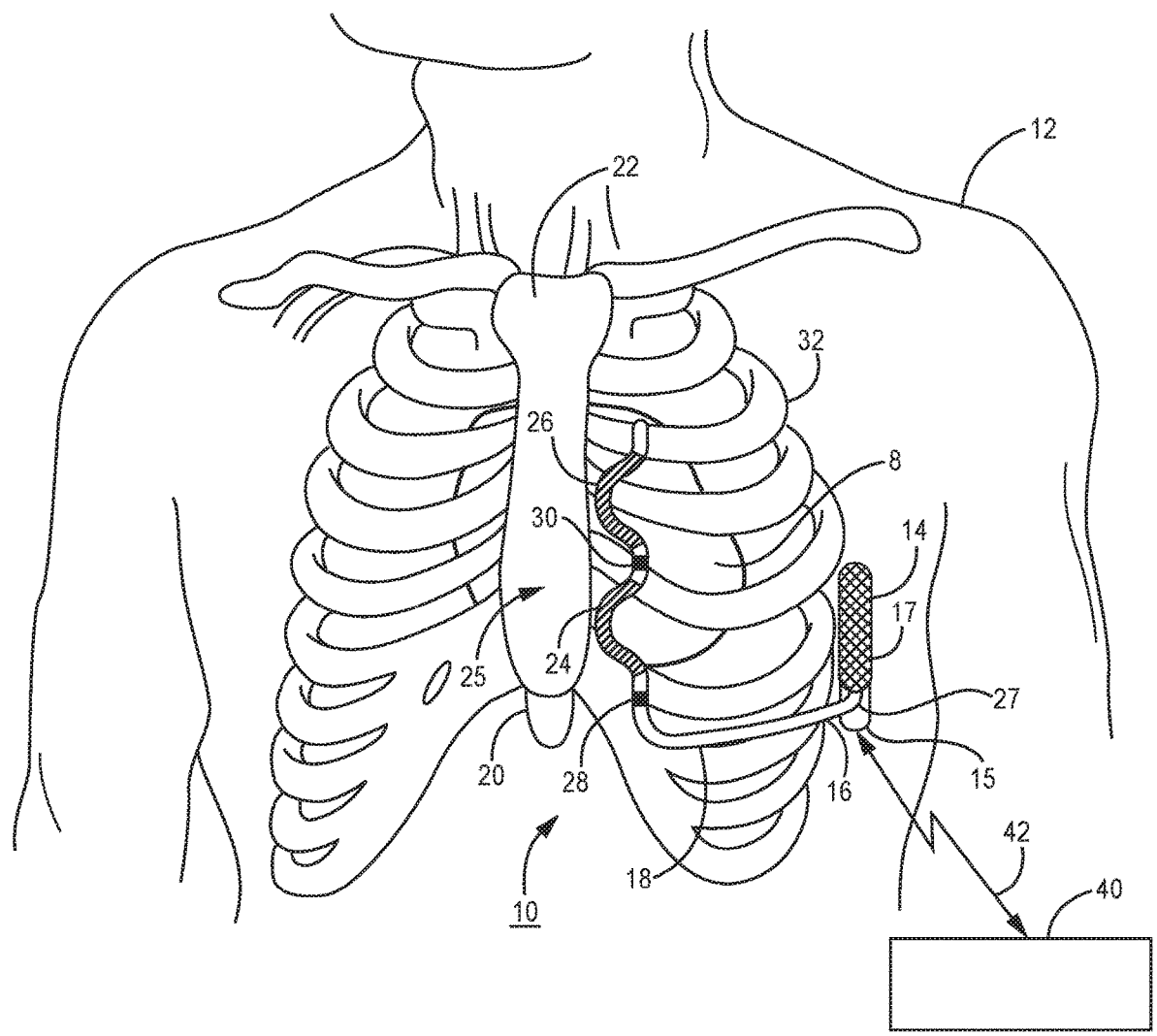
FIGS. 1A and 1B are conceptual diagrams of an extra-cardiovascular ICD system according to one example.
Figure 1B:
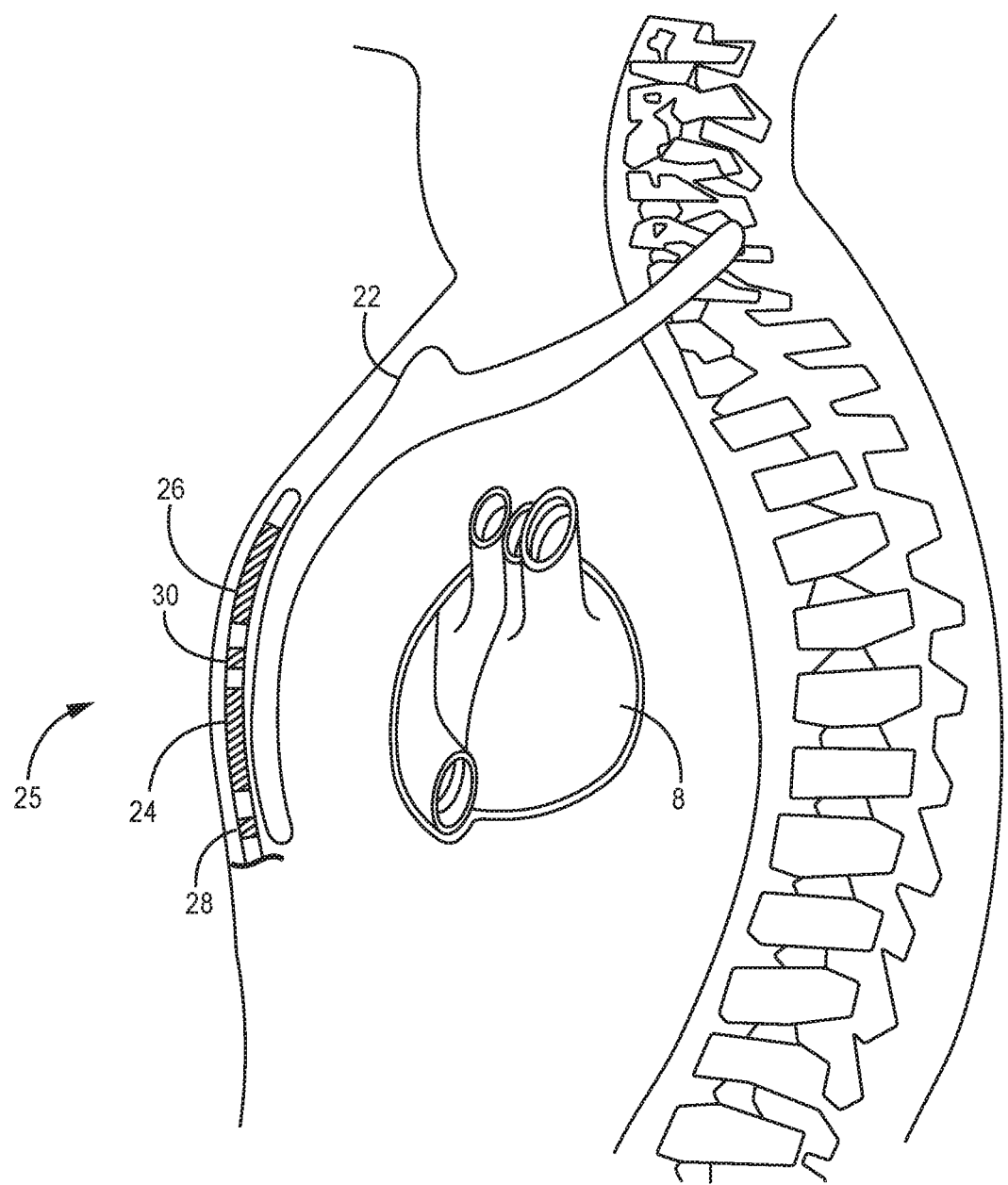

FIGS. 1A and 1B are conceptual diagrams of an extra-cardiovascular ICD system 10 according to one example. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a sensing vector used to sense cardiac electrical signals and detect and discriminate SVT, VT and VF.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage cardioversion defibrillation shocks. In some instances, electrodes 28 and 30 may provide only pacing functionality, only sensing functionality or both.

ICD 14 may obtain cardiac electrical signals corresponding to electrical activity of heart 8 via a combination of sensing vectors that include combinations of electrodes 24, 26, 28 and/or 30. In some examples, housing 15 of ICD 14 is used in combination with one or more of electrodes 24, 26, 28 and/or 30 in a sensing electrode vector. Various sensing electrode vectors utilizing combinations of electrodes 24, 26, 28, and 30 and housing 15 are described below for acquiring first and second cardiac electrical signals using respective first and second sensing electrode vectors that may be selected by sensing circuitry included in ICD 14.

In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at any location along lead body 18 and are not limited to the positions shown. In other examples, lead 16 may include none, one or more pace/sense electrodes and/or one or more defibrillation electrodes.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18 are each electrically coupled with respective defibrillation electrodes 24 and 26 and pace/sense electrodes 28 and 30, which may be separate respective insulated conductors within the lead body 18. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit sensed electrical signals from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in pending U.S. Pat. Publication No. 2016/0158567 (Marshall, et al.), incorporated herein by reference in its entirety. The techniques disclosed herein are not limited to any particular lead body design, however. In other examples, lead body 18 is a flexible elongated lead body without any pre-formed shape, bends or curves. Various example configurations of extra-cardiovascular leads and electrodes and dimensions that may be implemented in conjunction with the SVT discrimination techniques disclosed herein are described in pending U.S. Publication No. 2015/0306375 (Marshall, et al.) and pending U.S. Publication No. 2015/0306410 (Marshall, et al.), both of which are incorporated herein by reference in their entirety.

ICD 14 analyzes the cardiac electrical signals received from one or more sensing electrode vectors to monitor for abnormal rhythms, such as bradycardia, SVT, VT or VF. ICD 14 may analyze the heart rate and morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated herein by reference in its entirety. Example techniques for detecting VT and VF are described below in conjunction with the accompanying figures. The techniques for discriminating SVT from VT or VF for withholding a VT or VF detection as disclosed herein may be incorporated in a variety of VT/VF detection algorithms. Examples of devices and tachyarrhythmia detection algorithms that may be adapted to utilize techniques for SVT discrimination described herein are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

ICD 14 generates and delivers electrical stimulation therapy in response to detecting a tachyarrhythmia (e.g., VT or VF) using a therapy delivery electrode vector which may be selected from any of the available electrodes 24, 26, 28 30 and/or housing 15. ICD 14 may deliver ATP in response to VT detection, and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

FIGS. 1A and 1B are illustrative in nature and should not be considered limiting of the practice of the techniques disclosed herein. ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program cardiac event sensing parameters (e.g., R-wave sensing parameters), cardiac rhythm detection parameters (e.g., VT and VF detection parameters and SVT discrimination parameters) and therapy control parameters used by ICD 14. Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

Figure 2A:
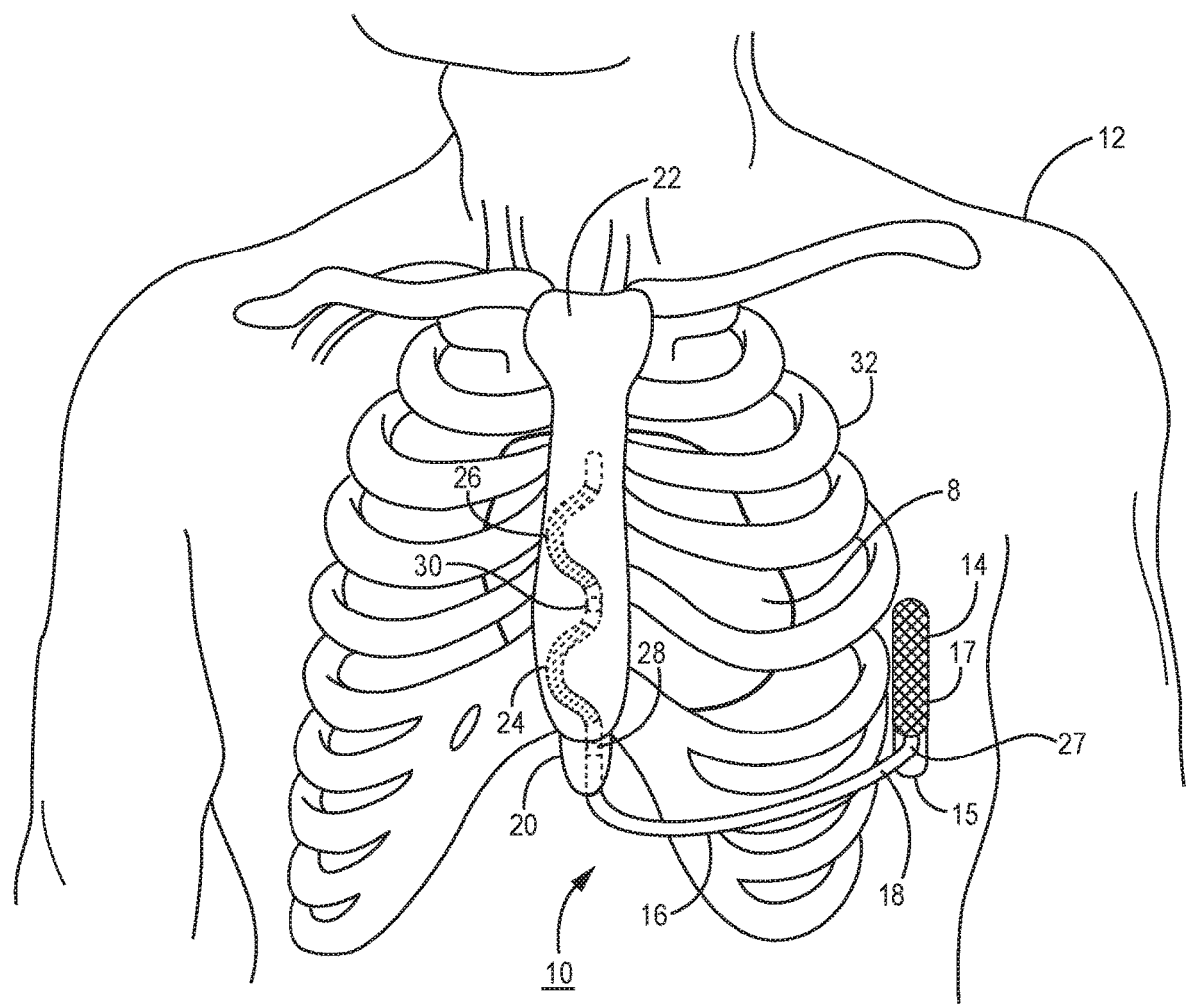
FIGS. 2A-2C are conceptual diagrams of a patient implanted with the extra-cardiovascular ICD system of FIG. 1A in a different implant configuration.
Figure 2B:
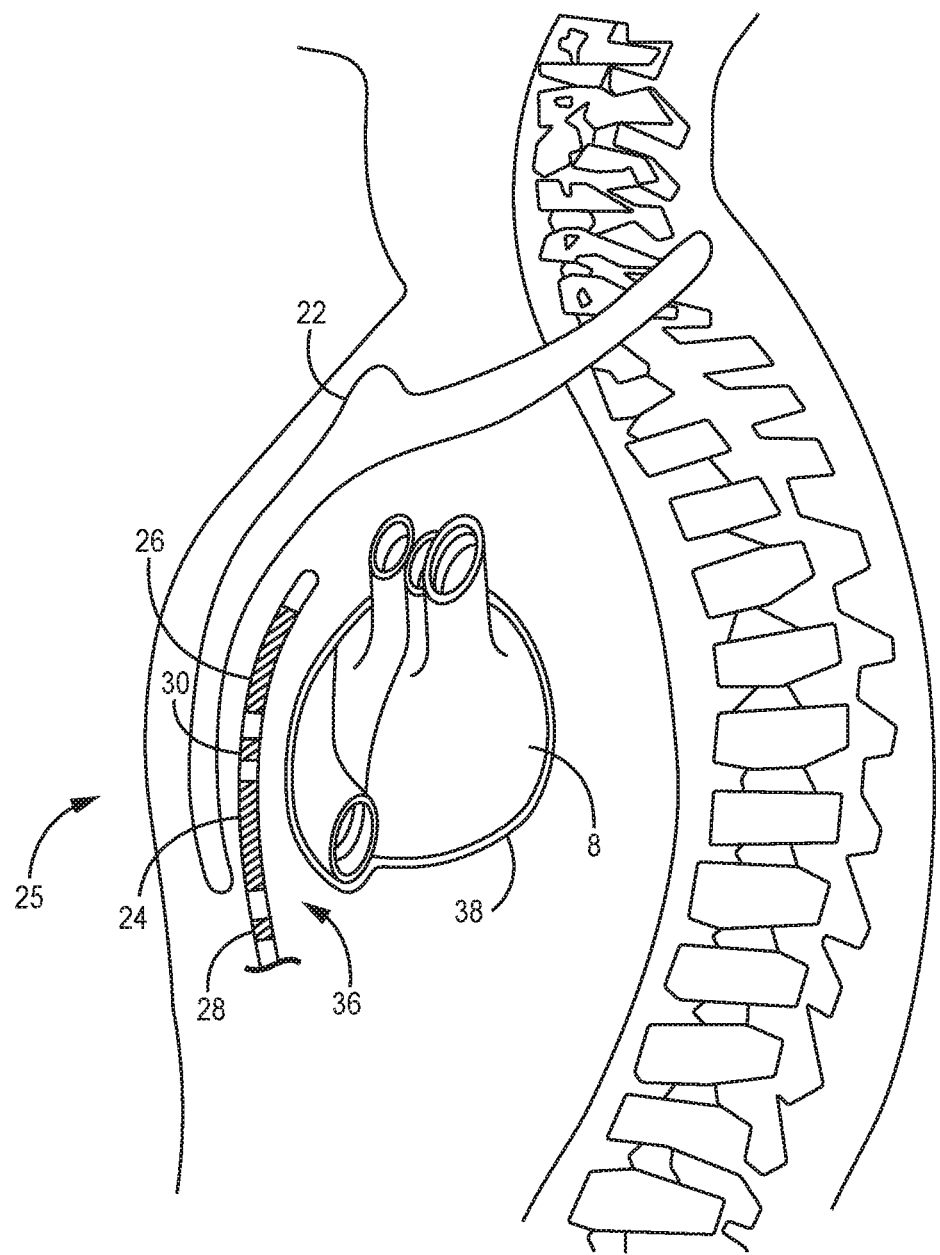
Figure 2C:
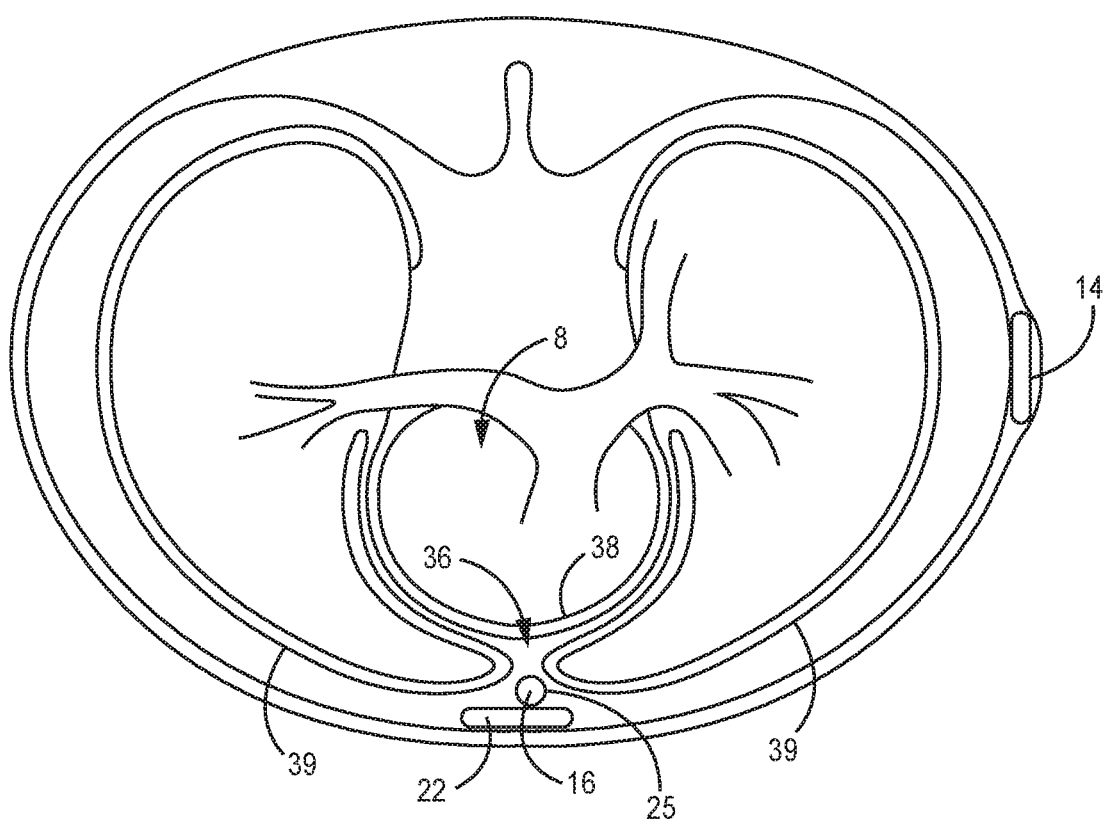

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 8. Other implant locations and lead and electrode arrangements that may be used in conjunction with the SVT discrimination techniques described herein are generally disclosed in the above-incorporated references.

Figure 3:
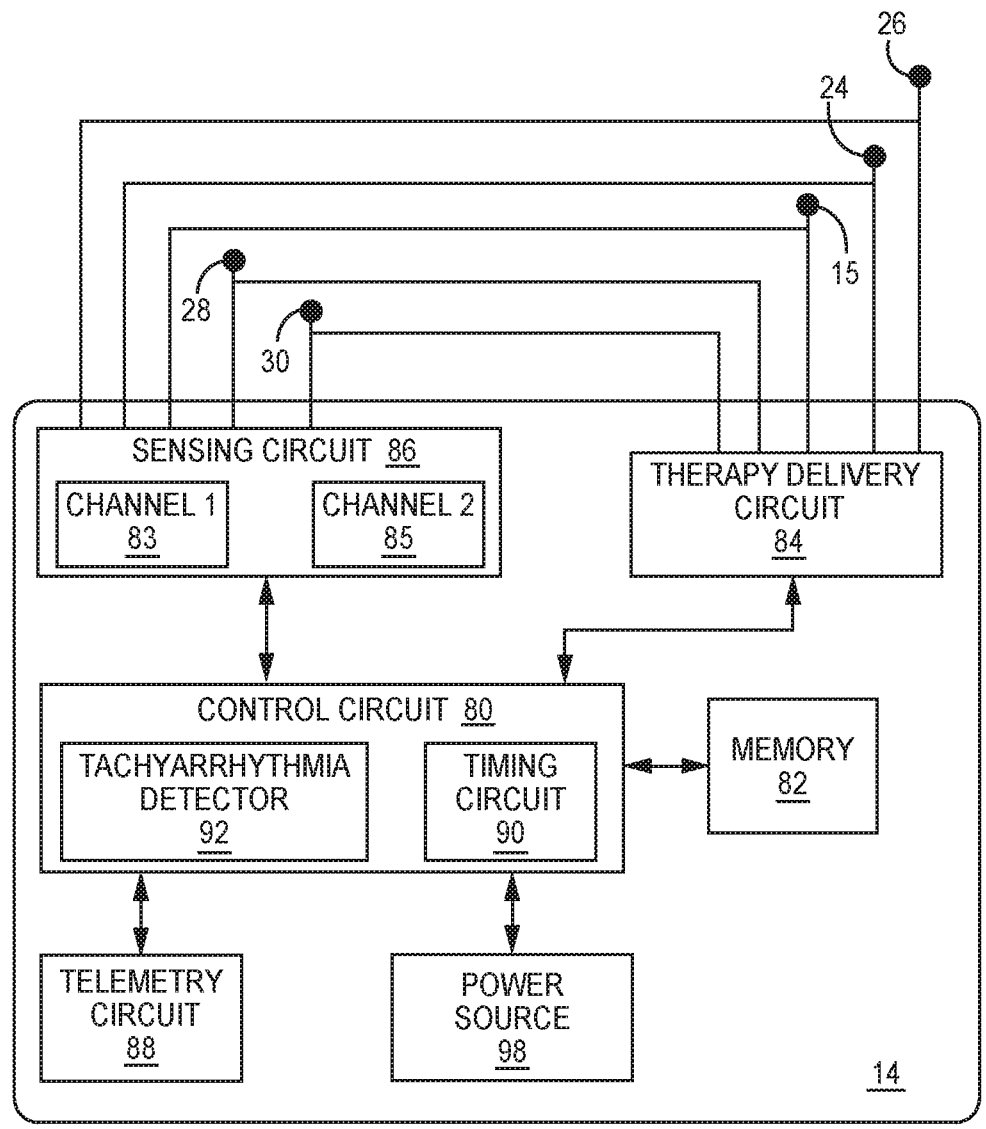
FIG. 3 is a schematic diagram of the ICD of FIGS. 1A-2C according to one example.

FIG. 3 is a schematic diagram of ICD 14 according to one example. The electronic circuitry enclosed within housing 15 (shown schematically as an electrode in FIG. 3) includes software, firmware and hardware that cooperatively monitor cardiac electrical signals, determine when an electrical stimulation therapy is necessary, and deliver therapies as needed according to programmed therapy delivery algorithms and control parameters. The software, firmware and hardware are configured to detect tachyarrhythmias and deliver anti-tachyarrhythmia therapy, e.g., detect ventricular tachyarrhythmias and in some cases discriminate VT from VF for determining when ATP or CV/DF shocks are required. ICD 14 is coupled to an extra-cardiovascular lead, such as lead 16 carrying extra-cardiovascular electrodes 24, 26, 28, and 30, for delivering electrical stimulation pulses to the patient's heart and for sensing cardiac electrical signals.

ICD 14 includes a control circuit 80, memory 82, therapy delivery circuit 84, sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 3, but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol, such as for bradycardia pacing, post-shock pacing, ATP and/or CV/DF shock pulses. Power source 98 is also coupled to components of sensing circuit 86, such as sense amplifiers, analog-to-digital converters, switching circuitry, etc. as needed.

The functional blocks shown in FIG. 3 represent functionality included in ICD 14 and may include any discrete and/or integrated electronic circuit components that implement analog and/or digital circuits capable of producing the functions attributed to ICD 14 herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

The functions attributed to ICD 14 herein may be embodied as one or more integrated circuits. Depiction of different features as circuits is intended to highlight different functional aspects and does not necessarily imply that such circuits must be realized by separate hardware or software components. Rather, functionality associated with one or more circuits may be performed by separate hardware, firmware or software components, or integrated within common hardware, firmware or software components. For example, cardiac event sensing and tachyarrhythmia detection operations may be performed cooperatively by sensing circuit 86 and control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 carried by lead 16 and the housing 15, which may function as a common or ground electrode or as an active can electrode for delivering CV/DF shock pulses or cardiac pacing pulses.

Sensing circuit 86 may be selectively coupled to electrodes 28, 30 and/or housing 15 in order to monitor electrical activity of the patient's heart. Sensing circuit 86 may additionally be selectively coupled to defibrillation electrodes 24 and/or 26 for use in a sensing electrode vector together or in combination with one or more of electrodes 28, 30 and/or housing 15. Sensing circuit 86 may be enabled to selectively receive cardiac electrical signals from at least two sensing electrode vectors from the available electrodes 24, 26, 28, 30, and housing 15. At least two cardiac electrical signals from two different sensing electrode vectors may be received simultaneously by sensing circuit 86. Sensing circuit 86 may monitor one or both or the cardiac electrical signals at a time for sensing cardiac electrical events, e.g., P-waves attendant to the depolarization of the atrial myocardium and/or R-waves attendant to the depolarization of the ventricular myocardium, and providing digitized cardiac signal waveforms for analysis by control circuit 80. For example, sensing circuit 86 may include switching circuitry (not shown) for selecting which of electrodes 24, 26, 28, 30, and housing 15 are coupled to a first sensing channel 83 and which are coupled to a second sensing channel 85 of sensing circuit 86. Switching circuitry may include a switch array, switch matrix, multiplexer, or any other type of switching device suitable to selectively couple components of sensing circuit 86 to selected electrodes.

Each sensing channel 83 and 85 may be configured to amplify, filter and digitize the cardiac electrical signal received from selected electrodes coupled to the respective sensing channel to improve the signal quality for detecting cardiac electrical events, such as R-waves or performing other signal analysis. The cardiac event detection circuitry within sensing circuit 86 may include one or more sense amplifiers, filters, rectifiers, threshold detectors, comparators, analog-to-digital converters (ADCs), timers or other analog or digital components as described further in conjunction with FIG. 4. A cardiac event sensing threshold may be automatically adjusted by sensing circuit 86 under the control of control circuit 80, based on timing intervals and sensing threshold values determined by control circuit 80, stored in memory 82, and/or controlled by hardware, firmware and/or software of control circuit 80 and/or sensing circuit 86.

Upon detecting a cardiac electrical event based on a sensing threshold crossing, sensing circuit 86 may produce a sensed event signal, such as an R-wave sensed event signal, that is passed to control circuit 80. In some examples, the sensed event signal may be used by control circuit 80 to trigger storage of a segment of a cardiac electrical signal for analysis for confirming the R-wave sensed event signals and discriminating SVT as described below.

The R-wave sensed event signals are also used by control circuit 80 for determining RR intervals (RRIs) for detecting tachyarrhythmia and determining a need for therapy. An RRI is the time interval between two consecutively sensed R-waves and may be determined between two consecutive R-wave sensed event signals received from sensing circuit 86. For example, control circuit 80 may include a timing circuit 90 for determining RRIs between consecutive R-wave sensed event signals received from sensing circuit 86 and for controlling various timers and/or counters used to control the timing of therapy delivery by therapy delivery circuit 84. Timing circuit 90 may additionally set time windows such as morphology template windows, morphology analysis windows or perform other timing related functions of ICD 14 including synchronizing CV/DF shocks or other therapies delivered by therapy delivery circuit 84 with sensed cardiac events. Tachyarrhythmia detector 92 is configured to analyze signals received from sensing circuit 86 for detecting tachyarrhythmia episodes. Tachyarrhythmia detector 92 may be implemented in control circuit 80 as software, hardware and/or firmware that processes and analyzes signals received from sensing circuit 86 for detecting VT and/or VF. In some examples, tachyarrhythmia detector 92 may include comparators and counters for counting RRIs determined by timing circuit 92 that fall into various rate detection zones for determining a ventricular rate or performing other rate- or interval-based assessments for detecting and discriminating VT and VF. For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 92.

When a VT or VF interval counter reaches a threshold count value, often referred to as "number of intervals to detect" or "NID," a ventricular tachyarrhythmia may be detected by control circuit 80. Tachyarrhythmia detector 92 may be configured to perform other signal analysis for determining if other detection criteria are satisfied before detecting VT or VF when an NID is reached however. For example, cardiac signal analysis may be performed to determine if R-wave morphology criteria, onset criteria, and noise and oversensing rejection criteria are satisfied in order to determine if the VT/VF detection should be made or withheld. As disclosed herein, tachyarrhythmia detector 92 may withhold the VT or VF detection when an NID is reached if analysis of cardiac signal waveform features indicates that the rhythm is an SVT rhythm.

To support additional cardiac signal analyses performed by tachyarrhythmia detector 92, sensing circuit 86 may pass a digitized cardiac electrical signal to control circuit 80. A cardiac electrical signal from the selected sensing channel, e.g., from first sensing channel 83 and/or the second sensing channel 85, may be passed through a filter and amplifier, provided to a multiplexer and thereafter converted to multibit digital signals by an analog-to-digital converter, all included in sensing circuit 86, for storage in memory 82.

Memory 82 may include read-only memory (ROM) in which stored programs controlling the operation of the control circuit 80 reside. Memory 82 may further include random access memory (RAM) or other memory devices configured as a number of recirculating buffers capable of holding a series of measured RRIs, counts or other data for analysis by the tachyarrhythmia detector 92. Memory 82 may be configured to store a predetermined number of cardiac electrical signal segments in circulating buffers under the control of control circuit 80. For instance, up to eight cardiac electrical signal segments each corresponding to an R-wave sensed event signal may be stored in memory 82. Additionally or alternatively, features derived from each of up to eight cardiac signal segments that each correspond to an R-wave sensed event signal may be buffered in memory 82 for use in SVT discrimination as described below.

Therapy delivery circuit 84 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Timing circuit 90 of control circuit 80 may include various timers or counters that control when ATP or other cardiac pacing pulses are delivered. For example, timing circuit 90 may include programmable digital counters set by a microprocessor of the control circuit 80 for controlling the basic pacing time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

In response to detecting VT or VF, control circuit 80 may control therapy delivery circuit 84 to deliver therapies such as ATP and/or CV/DF therapy. Therapy can be delivered by initiating charging of high voltage capacitors via a charging circuit, both included in therapy delivery circuit 84. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line and passed to therapy delivery circuit 84, terminating charging. A CV/DF pulse is delivered to the heart under the control of the timing circuit 90 by an output circuit of therapy delivery circuit 84 via a control bus. The output circuit may include an output capacitor through which the charged high voltage capacitor is discharged via switching circuitry, e.g., an H-bridge, which determines the electrodes used for delivering the cardioversion or defibrillation pulse and the pulse wave shape. In some examples, the high voltage therapy circuit configured to deliver CV/DF shock pulses can be controlled by control circuit 80 to deliver pacing pulses, e.g., for delivering ATP or post shock pacing pulses. In other examples, therapy delivery circuit 84 may include a low voltage therapy circuit for generating and delivering relatively lower voltage pacing pulses for a variety of pacing needs. Therapy delivery and control circuitry generally disclosed in any of the above-incorporated patents may be implemented in ICD 14.

It is recognized that the methods disclosed herein may be implemented in an implantable medical device that is used for monitoring cardiac electrical signals by sensing circuit 86 and control circuit 80 without having therapy delivery capabilities or in an implantable medical device that monitors cardiac electrical signals and delivers cardiac pacing therapies by therapy delivery circuit 84, without high voltage therapy capabilities, such as cardioversion/defibrillation shock capabilities or vice versa.

Control parameters utilized by control circuit 80 for detecting cardiac arrhythmias and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Figure 4:
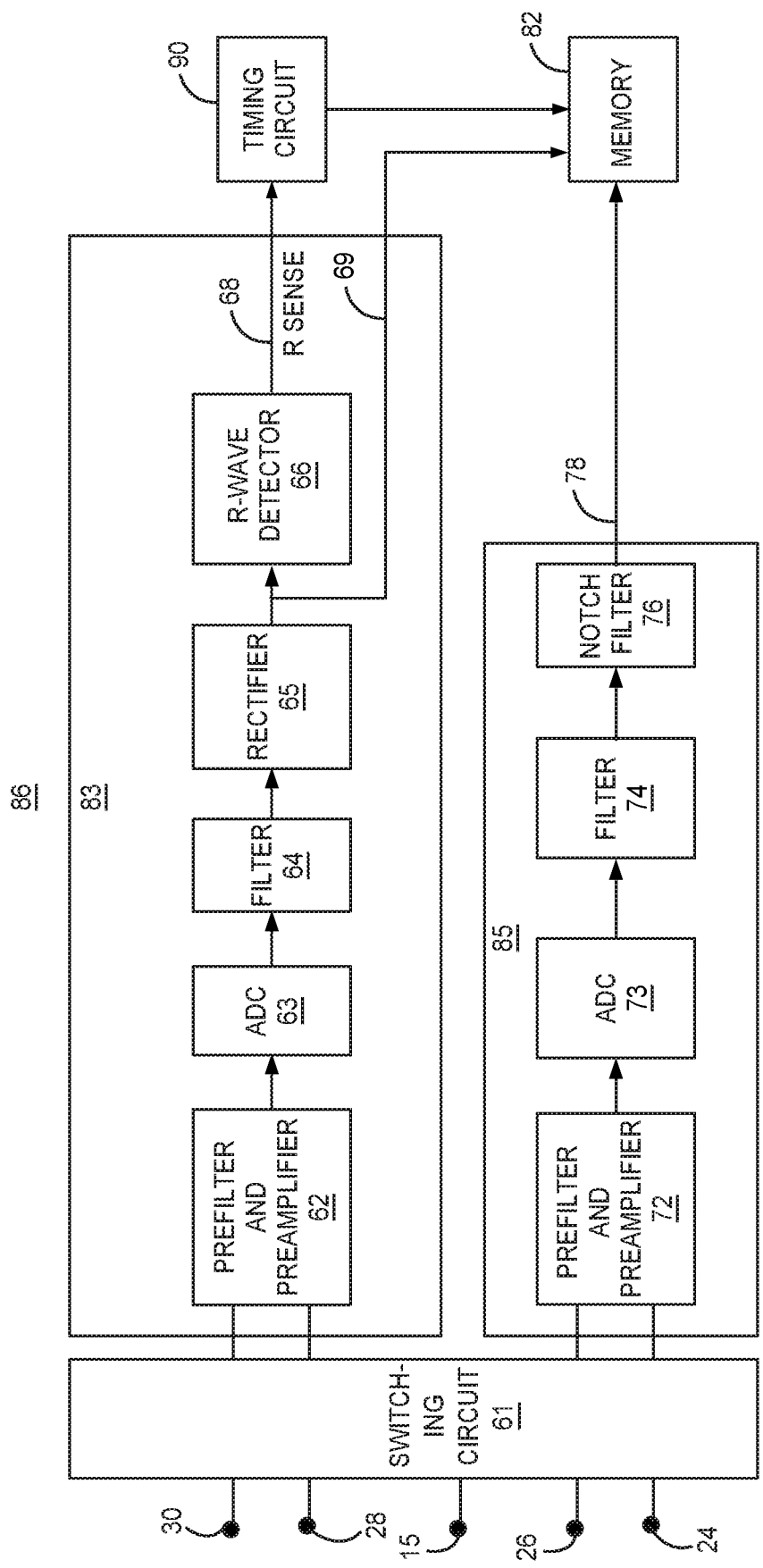
FIG. 4 is diagram of circuitry included in the sensing circuit of FIG. 3 according to one example.

FIG. 4 is a diagram of circuitry included in first sensing channel 83 and second sensing channel 85 of sensing circuit 86 according to one example. First sensing channel 83 may be selectively coupled via switching circuitry 61 to a first sensing electrode vector including electrodes carried by extra-cardiovascular lead 16 as shown in FIGS. 1A-20 for receiving a first cardiac electrical signal. First sensing channel 83 may be coupled to a sensing electrode vector that is a short bipole, having a relatively shorter inter-electrode distance or spacing than the second electrode vector coupled to second sensing channel 85. For example, the first sensing electrode vector may include pace/sense electrodes 28 and 30. In other examples, the first sensing electrode vector coupled to sensing channel 83 may include a defibrillation electrode 24 and/or 26, e.g., a sensing electrode vector between pace/sense electrode 28 and defibrillation electrode 24 or between pace/sense electrode 30 and either of defibrillation electrodes 24 or 26. In still other examples, the first sensing electrode vector may be between defibrillation electrodes 24 and 26.

In some patients, a bipole between electrodes carried by lead 16 may result in patient body posture dependent changes in the cardiac electrical signal as the sensing vector of the bipole relative to the cardiac axis changes with changes in patient body posture or body motion. Accordingly, the sensing electrode vector coupled to the first sensing channel 83 may include housing 15 and any of the electrodes 24, 26, 28 and 30 carried by lead 16. A relatively longer bipole including housing 15 and a lead-based electrode may be less sensitive to positional changes. Cardiac electrical signals received via extra-cardiovascular electrodes may be influenced by positional changes of the patient than electrodes carried by transvenous leads. The amplitude, polarity, and wave shape of R-waves may change, for example, as patient posture changes. As a result, R-wave morphology analysis performed to discriminate between SVT and VT/VF may lead to false VT/VF detection when R-wave amplitude and/or morphology has changed due to positional changes of the patient. The techniques disclosed herein may be used to detect and discriminate SVT to avoid false detection of VT and VF and unnecessary electrical stimulation therapies even when patient posture changes cause changes in QRS amplitude and morphology.

Sensing circuit 86 includes a second sensing channel 85 that receives a second cardiac electrical signal from a second sensing vector, for example from a vector that includes a pace/sense electrode 28 or 30 paired with housing 15. Second sensing channel 85 may be selectively coupled to other sensing electrode vectors, which may form a relatively long bipole having an inter-electrode distance or spacing that is greater than the sensing electrode vector coupled to first sensing channel 83 in some examples. As described below, the second cardiac electrical signal received by second sensing channel 85 via a long bipole may be used by control circuit 80 for morphology analysis and for determining cardiac signal segment features for use in SVT discrimination. In other examples, any vector selected from the available electrodes, e.g., electrodes 24, 26, 28, 30 and/or housing 15, may be included in a sensing electrode vector coupled to second sensing channel 85. The sensing electrode vectors coupled to first sensing channel 83 and second sensing channel 85 are typically different sensing electrode vectors, which may have no common electrodes or only one common electrode but not both.

In the illustrative example shown in FIG. 4, the electrical signals developed across a first sensing electrode vector are received by sensing channel 83 and electrical signals developed across a second sensing electrode vector are received by sensing channel 85. The cardiac electrical signals are provided as differential input signals to the pre-filter and pre-amplifiers 62 and 72, respectively, of first sensing channel 83 and second sensing channel 85. Non-physiological high frequency and DC signals may be filtered by a low pass or bandpass filter included in each of pre-filter and pre-amplifiers 62 and 72, and high voltage signals may be removed by protection diodes included in pre-filter and pre-amplifiers 62 and 72. Pre-filter and pre-amplifiers 62 and 72 may amplify the pre-filtered signal by a gain of between 10 and 100, and in one example a gain of 17.5, and may convert the differential signal to a single-ended output signal passed to analog-to-digital converter (ADC) 63 in first sensing channel 83 and to ADC 73 in second sensing channel 85. Pre-filters and amplifiers 62 and 72 may provide anti-alias filtering and noise reduction prior to digitization.

ADC 63 and ADC 73, respectively, convert the first cardiac electrical signal from an analog signal to a first digital bit stream and the second cardiac electrical signal to a second digital bit stream. In one example, ADC 63 and ADC 73 may be sigma-delta converters (SDC), but other types of ADCs may be used. In some examples, the outputs of ADC 63 and ADC 73 may be provided to decimators (not shown), which function as digital low-pass filters that increase the resolution and reduce the sampling rate of the respective first and second cardiac electrical signals.

In first sensing channel 83, the digital output of ADC 63 is passed to filter 64 which may be a digital bandpass filter having a bandpass of approximately 10 Hz to 30 Hz for passing cardiac electrical signals such as R-waves typically occurring in this frequency range. The bandpass filtered signal is passed from filter 64 to rectifier 65 then to R-wave detector 66. In some examples, the filtered, digitized cardiac electrical signal from sensing channel 83, e.g., output of filter 64 or rectifier 65, may be stored in memory 82 for signal processing by control circuit 80 for use in detecting and discriminating tachyarrhythmia episodes.

R-wave detector 66 may include an auto-adjusting sense amplifier, comparator and/or other detection circuitry that compares the filtered and rectified first cardiac electrical signal to an R-wave sensing threshold in real time and produces an R-wave sensed event signal 68 when the cardiac electrical signal crosses the R-wave sensing threshold outside of a post-sense blanking period.

The R-wave sensing threshold, controlled by sensing circuit 86 and/or control circuit 80, may be a multi-level sensing threshold as disclosed in pending U.S. patent application Ser. No. 15/142,171 (Cao, et al., filed on Apr. 29, 2016), incorporated herein by reference in its entirety. Briefly, the multi-level sensing threshold may have a starting sensing threshold value held for a time interval, which may be equal to a tachycardia detection interval or expected R-wave to T-wave interval, then drops to a second sensing threshold value held until a drop time interval expires, which may be 1 to 2 seconds long. The sensing threshold drops to a minimum sensing threshold, which may correspond to a programmed sensitivity, after the drop time interval. In other examples, the R-wave sensing threshold used by R-wave detector 66 may be set to a starting value based on the most-recently sensed R-wave peak amplitude and decay linearly or exponentially over time until reaching a minimum sensing threshold. The techniques described herein are not limited to a specific behavior of the sensing threshold. Instead, other decaying, step-wise adjusted or other automatically adjusted sensing thresholds may be utilized.

The second cardiac electrical signal, digitized by ADC 73 of sensing channel 85, may be passed to filter 74 for bandpass filtering. In some examples, filter 74 is a wideband filter for passing frequencies from 1 to 30 Hz or higher. In some examples, sensing channel 85 includes notch filter 76. Notch filter 76 may be implemented in firmware or hardware and to attenuate 50 Hz or 60 Hz electrical noise in the second cardiac electrical signal. Cardiac electrical signals acquired using extra-cardiovascular electrodes may be more susceptible to 50 to 60 Hz electrical noise than transvenous or intra-cardiac electrodes, muscle noise and other EMI, electrical noise or artifacts. As such, notch filter 76 may be provided to significantly attenuate the magnitude of signals in the range of 50-60 Hz with minimum attenuation of signals in the range of approximately 1-30 Hz, corresponding to typical cardiac electrical signal frequencies.

The output signal 78 of notch filter 76 may be passed from sensing circuit 86 to memory 82 under the control of control circuit 80 for storing segments of the second cardiac electrical signal 78 in temporary buffers of memory 82. For example, timing circuit 90 of control circuit 80 may set a time interval or number of sample points relative to an R-wave sensed event signal 68 received from first sensing channel 83, over which the second cardiac electrical signal 78 is stored in memory 82. The buffered, second cardiac electrical signal segment may be analyzed by control circuit 80 on a triggered, as needed basis, e.g., as described in conjunction with FIG. 13, for determining cardiac signal segment features for discriminating SVT and withholding an interval-based VT or VF detection, even when other R-wave morphology analysis meets VT/VF detection criteria.

Notch filter 76 may be implemented as a digital filter for real-time filtering performed by firmware as part of sensing channel 85 or by control circuit 80 for filtering the buffered digital output of filter 74. In some examples, the output of filter 74 of sensing channel 85 may be stored in memory 82 in time segments defined relative to an R-wave sensed event signal 68 prior to filtering by notch filter 76. When control circuit 80 is triggered to buffer and analyze segments of the second cardiac electrical signal, for example as described in conjunction with FIG. 13, the notch filter 76 may be applied to the second cardiac electrical before morphology analysis and determination of cardiac signal segment features used for SVT discrimination.

The configuration of sensing channels 83 and 85 shown in FIG. 4 is illustrative in nature and should not be considered limiting of the techniques described herein. The sensing channels 83 and 85 of sensing circuit 86 may include more or fewer components than illustrated and described in FIG. 4. First sensing channel 83 may be configured to detect R-waves from a first cardiac electrical signal in real time, e.g., in hardware implemented components, based on crossings of an R-wave sensing threshold by the first cardiac electrical signal, and second sensing channel 85 may be configured to provide a second cardiac electrical signal for storage in memory 82 for processing and analysis by control circuit 80 for determining if the signal waveform morphology corresponding to a sensed R-wave in the first sensing channel is indicative of VT or VF or if the signal waveform features support an SVT detection and withholding of VT or VF detection. In other examples, both sensing channels 83 and 85 may be capable of sensing R-waves in real time and/or both channels 83 and 85 may provide a digitized cardiac signal for buffering in memory 82 for morphological signal analysis during VT/VF detection algorithms.

Figure 5:
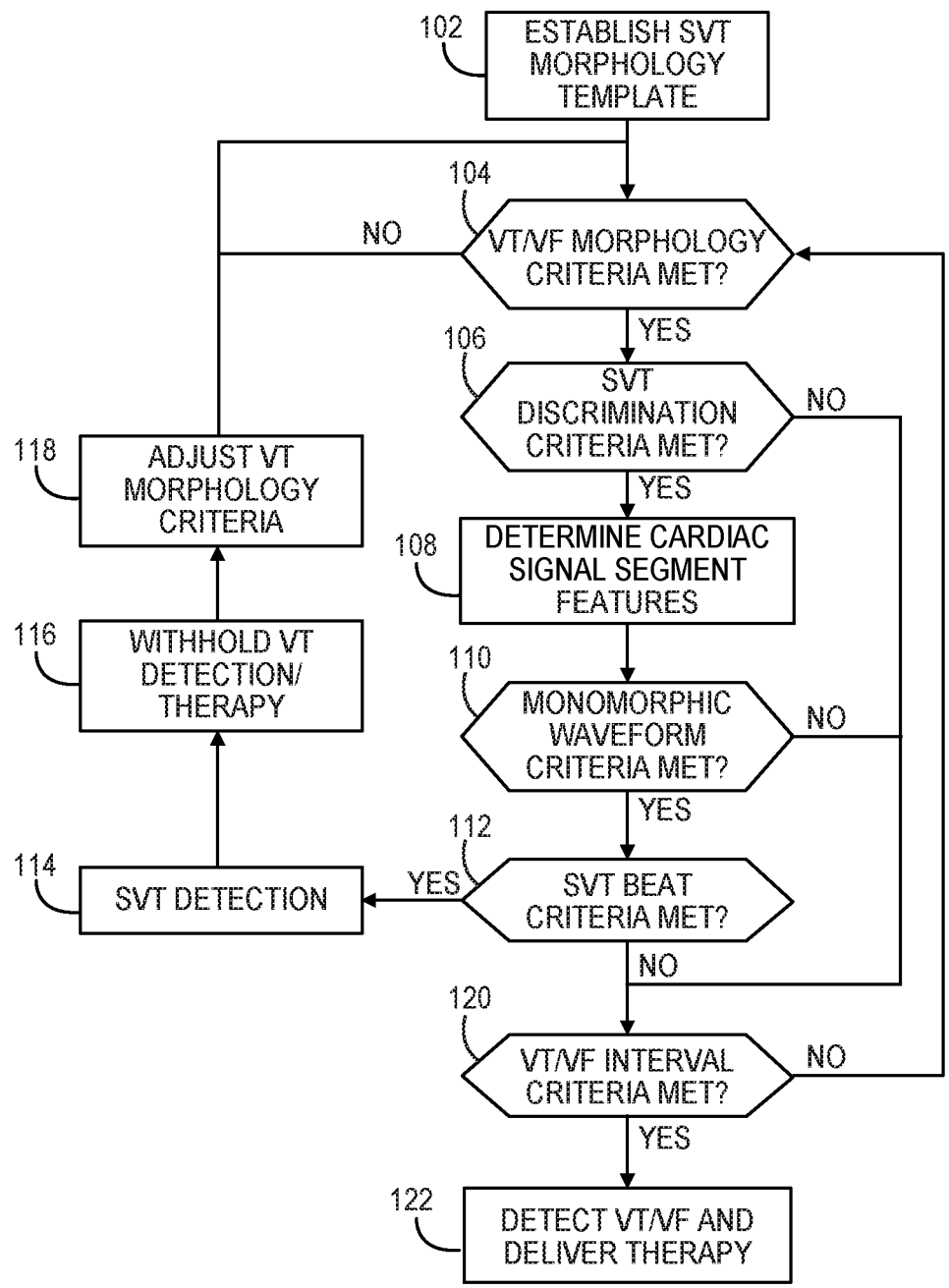
FIG. 5 is a flow chart of a method performed by an ICD for discriminating SVT from a ventricular tachyarrhythmia according to one example.

FIG. 5 is a flow chart 100 of a method performed by ICD 14 for discriminating SVT from a ventricular tachyarrhythmia according to one example. The flow chart 100 provides a technique for discriminating SVT from VT/VF, even when certain VT/VF morphology criteria are met, to account for QRS morphology changes that may occur due to changes in patient posture in an extra-vascular ICD system. The techniques for SVT discrimination may be usefully practiced in other ICDs or other medical device systems as well and are not necessarily limited to implantable, extra-cardiovascular systems. The techniques of flow chart 100 may be implemented in conjunction with a variety of VT/VF detection algorithms for causing VT/VF detection to be withheld when SVT discrimination criteria are satisfied, even though other VT/VF detection criteria may be satisfied, such as RRI-based detection criteria and/or R-wave morphology-based VT/VF detection criteria.

At block 102, control circuit 80 establishes an SVT morphology template. The morphology template may be established according to techniques disclosed in the above-incorporated U.S. Pat. No. 6,393,316 (Gillberg, et al.), and as generally described below in conjunction with FIG. 6. The SVT morphology template represents the expected R-wave morphology during a supraventricular rhythm, which may be a sinus rhythm or an atrial tachyarrhythmia that is conducted to the ventricles. While referred to herein as an "SVT" template, the template may be acquired during a slow, non-paced ventricular rhythm to represent a normal QRS waveform arising from the sinus node and is not necessarily acquired during supraventricular tachycardia. In other examples, the SVT template may be acquired during sinus tachycardia, for example during patient exercise.

At block 104, control circuit 80 compares the SVT template to the morphology of waveforms of the cardiac electrical signal received from sensing circuit 86 corresponding to sensed R-waves. This comparison may be made on a continuous beat-by-beat basis or only when other conditions are met, such as an increase in heart rate. This morphology comparison may be performed using a wavelet transform technique as generally disclosed in the above-incorporated '316 patent. The comparison determines a morphology match score that is a measure of the correlation between the SVT morphology template and the unknown cardiac electrical signal waveform which may be stored in memory in response to a sensed R-wave. For example, a Haar transform or other wavelet transform technique may generate a set of wavelet coefficients for the signal waveform. The wavelet coefficients may have predetermined weightings representative of the amplitudes of the frequency components of a signal waveform. These wavelet coefficients may be compared to wavelet coefficients determined from the SVT template and the morphology match score may represent the correlation between the wavelet coefficients of the SVT template and the unknown signal waveform. A match score threshold may be defined, below which the unknown cardiac signal waveform is not considered to be an R-wave corresponding to an supraventricular rhythm and above which the waveform is considered to be an R-wave of a supraventricular rhythm. In one example, if the morphology match score may range from 1 to 100, and the morphology match score may be set to 60, 70 or another predetermined value.

At block 104, control circuit 80 determines if morphology criteria for detecting VT/VF are met based on morphology comparisons between the SVT template and unknown cardiac signal waveforms received by control circuit 80 from sensing circuit 86 and corresponding to R-wave sensed event signals. VT/VF morphology criteria may be defined for determining if the cardiac signal is likely to represent a rhythm originating in the ventricles. In one example, the VT/VF morphology criteria may require that a predetermined percentage or ratio of R-wave sensed event signals be classified as non-SVT beats based on morphology analysis of cardiac signal waveforms corresponding to each R-wave sensed event signal. An R-wave sensed event signal may be classified as either an SVT beat or a non-SVT beat based on the most recent Y morphology matching scores of the unknown cardiac signal waveforms.

For example, if at least 6 out of 8 of the most recently acquired cardiac signal waveforms, each corresponding to an R-wave sensed event signal, do not match the SVT morphology template, based on a morphology match score being less than the match threshold, the latest one of the R-wave sensed event signals of the group of 8 sensed event signals is classified as a potential VT/VF beat. When a threshold number of R-wave sensed event signals are classified as potential VT/VF beats, VT/VF morphology criteria may be satisfied at block 104. The threshold number of R-wave sensed events being classified as potential VT/VF beats required to satisfy the VT/VF morphology criteria may be one or more and may be dynamically adjusted by control circuit 80, e.g., as described in conjunction with FIG. 10.

Each of the eight (or other predetermined number of) cardiac signal waveforms used to classify a given R-wave sensed event signal as a potential VT/VF beat may be obtained from a cardiac electrical signal segment that is buffered in memory 82 from the second cardiac electrical signal received from the second sensing channel 85 of sensing circuit 86. These cardiac signal segments may be acquired over a time interval set based on the timing of an R-wave sensed event signal produced by the first sensing channel 83. As described below, the buffering of these cardiac signal segments, each corresponding to an R-wave sensed event signal produced by the first sensing channel 83, may be triggered at block 104 when control circuit 80 determines that specified conditions are met, e.g., when evidence of a fast ventricular rate has been detected based on a predetermined number of VT or VF intervals being counted.

If VT/VF morphology criteria are not met at block 104, control circuit 80 continues to monitor the cardiac electrical signal for evidence of VT/VF morphology by analyzing buffered cardiac signal segments corresponding to R-wave sensed event signals. If the VT/VF morphology criteria are satisfied at block 104, control circuit 80 determines if criteria for enabling SVT discrimination are satisfied at block 106. In one example, criteria for enabling SVT discrimination requires that the VT/VF morphology criteria are met at block 104 and that at least X out of Y most recent cardiac signal waveforms match the SVT morphology template with a matching score that is greater than a second match threshold. The second match threshold is less than the first, morphology match threshold applied at block 104 for classifying R-wave sensed events as potential VT/VF. In one example, if the first match threshold applied at block 104 is 60, the second match threshold applied at block 106 is 20.

To illustrate, if cardiac signal waveforms are required to have a matching score that is less than a match threshold of 60 according to VT/VF morphology criteria at block 104, SVT discrimination may be enabled at block 106 when VT/VF morphology criteria are met and at least 6 out of 8 most recent cardiac signal waveforms corresponding to R-wave sensed event signals match the SVT morphology template with a matching score of at least 20. SVT discrimination may be enabled when the morphology matching scores of the most recent group of cardiac signal waveforms are not highly correlated with the SVT template (less than first match threshold), suggesting a ventricular tachyarrhythmia, but are greater than a second, lower match threshold. The QRS morphology during a supraventricular rhythm may change compared to the SVT template, e.g., due to postural changes of the patient, causing the morphology matching scores to be less than the first match threshold. In order to avoid a false VT/VF detection due to a change in QRS morphology during an SVT rhythm, SVT discrimination is enabled at block 106 if the morphology match scores that led to the VT/VF morphology criteria being met are at least greater than the second match threshold.

On the other hand, very low morphology match scores that are less than the second match threshold indicate very low correlation to the SVT template. If fewer than 6 out of 8 (or other predetermined percentage), of the most recent cardiac signal segments have morphology match scores less than the second threshold, a likelihood of a VT/VF rhythm exists. In this case, SVT discrimination is not enabled. If criteria for enabling the SVT discrimination are not satisfied at block 106, the VT/VF morphology criteria satisfied at block 104 may be determined to be evidence of a tachyarrhythmia that is ventricular in origin and does not require further discrimination. Control circuit 80 advances toward VT/VF detection at block 120 without performing additional morphology analysis of the cardiac signal for discriminating SVT.

If criteria for enabling SVT discrimination are satisfied at block 106, e.g., if at least X of Y morphology match scores are greater than the second, lower morphology match threshold (but less than the first, higher match threshold), control circuit 80 begins determining multiple features of each of the buffered cardiac signal segments at block 108 for use in discriminating SVT from VT/VF. Determination of cardiac signal segment features is described below in conjunction with FIGS. 7-9. At block 110, a first portion of the cardiac signal segment features determined from each of one of a group of Y cardiac signal segments are compared to monomorphic waveform criteria. At block 112, a second portion of the cardiac signal segment features determined from each of the Y buffered signal segments are compared to SVT beat criteria.

If monomorphic waveform criteria and SVT beat criteria are satisfied at blocks 110 and 112, respectively, the rhythm may be identified as an SVT rhythm at block 114. A VT/VF detection indicated by the VT/VF morphology criteria being satisfied at block 104 is withheld at block 116, and VT/VF therapy is subsequently not delivered. At block 118, control circuit 80 may adjust the VT/VF morphology detection criteria to delay VT/VF detection if cardiac signal segments continue to fail to match the SVT template based on the first match threshold at block 104. For example, the number of R-wave sensed event signals required to be classified as potential VT/VF beats in order to satisfy the VT/VF morphology criteria at block 104 may be reset or adjusted at block 118, as described below in conjunction with FIG. 10.

In some examples, both the monomorphic waveform criteria and the SVT beat criteria are required to be satisfied at blocks 110 and 112 in order to detect SVT and withhold VT/VF detection and therapy. If either one of the monomorphic waveform criteria or the SVT beat criteria are not satisfied, SVT is not detected. Control circuit 80 advances to block 120, and, if VT or VF detection criteria are satisfied at block 120, VT or VF is detected at block 122. For example, if the VT/VF morphology criteria are satisfied at block 104, and an SVT detection is not made ("no" branch of block 112), control circuit 80 may detect VT or VF at block 122 if the respective VT or VF NID is reached at block 120. If interval-based VT/VF detection criteria are not satisfied at block 120, control circuit continues to monitor the cardiac electrical signal by returning to block 104.

If both the VT/VF morphology criteria and the VT/VF interval criteria are satisfied at respective blocks 104 and 120, and SVT beat criteria are not met at block 112 (or the SVT discriminator is not enabled at block 106), VT or VF is detected at block 122. An electrical stimulation therapy may be scheduled and delivered at block 122. The electrical stimulation therapy may include ATP and/or a CV/DF shock delivered by therapy delivery circuit 84 according to a programmed therapy protocol for the detected VT or VF rhythm.

The blocks shown in FIG. 5 may be performed in a different order than the particular order shown in FIG. 5. In other examples, morphology match scores and cardiac signal segment features may be determined at blocks 104 and 108 in response to a threshold number of RRIs falling into a VT or VF interval zone, indicating the possible onset of a fast heart rate. Control circuit 80 may determine if the monomorphic waveform criteria and the SVT beat criteria are met at blocks 110 and 112, respectively, in response to an NID being reached to determine if VT/VF detection should be made or withheld based on SVT discrimination criteria being met. In still other examples, the morphology match scores and/or cardiac signal segment features may be determined on a beat-by-beat basis such that, once an NID is reached, the VT or VF detection may be made as long as the monomorphic waveform and SVT beat criteria are unmet for at least the most recent group of Y cardiac signal segments.

Figure 6:
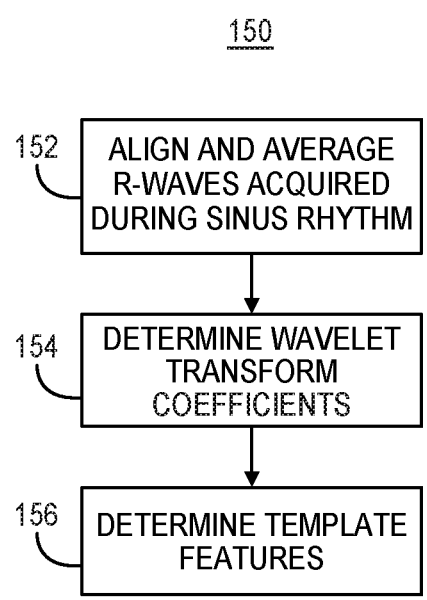
FIG. 6 is a flow chart of a method that may be performed by an ICD for establishing an SVT morphology template.

FIG. 6 is a flow chart 150 of a method that may be performed by control circuit 80 for establishing the SVT morphology template at block 102 of FIG. 5. At block 152, control circuit 80 may acquire a predetermined number of R-wave signals (or QRS complexes) from a cardiac electrical signal received from sensing circuit 86 during a known supraventricular rhythm. For example, a sinus rhythm may be confirmed manually by a user using external device 40 or automatically by detecting a normal heart rate (e.g., less than a tachyarrhythmia rate associated with VT/VF detection intervals) and/or regular, stable R-wave signals. For example, three or more R-wave signals may be acquired at block 152. These R-wave signals may be notch-filtered signals received from the second sensing channel 85, each corresponding to an R-wave sensed event signal received from the first sensing channel 83. The notch-filtered R-wave signal segments may be aligned in time relative to the time of the corresponding R-wave sensed event signal. In other examples, a different reference time point or sample number may be used to align the R-wave signal segments such as a maximum peak or other fiducial point. The notch-filtered R-wave signals may then be ensemble averaged to obtain an averaged R-wave signal to establish an SVT morphology template for use in determining if VT/VF morphology criteria are met at block 104 of FIG. 5. In other examples, the template may be generated from a single R-wave signal acquired during sinus rhythm.

At block 154, wavelet transform coefficients are determined from the averaged R-wave signal. Determination of wavelet transform coefficients may be performed according to the above-incorporated '316 patent (Gillberg, et al.). The digitized averaged R-wave signal and/or the wavelet transform coefficients may be stored in memory 82 as the SVT morphology template.

At block 156, template features are determined from the averaged R-wave signal. These template features are used when SVT discrimination is performed, e.g., if SVT discrimination criteria are met at block 106 of FIG. 5. In some examples, the template features determined at block 156 are used at block 112 of FIG. 5 for comparison to a portion of the signal waveform features determined from each cardiac signal segment of a group of Y cardiac signal segments. The template features may be compared to signal waveform features determined from cardiac signal segments when SVT discrimination is enabled for determining whether SVT beat criteria are met at block 112. The template features determined at block 156 may or may not be used in determining whether monomorphic waveform criteria are met at block 110 of FIG. 5. As described in conjunction with FIG. 11 below, a portion of the signal waveform features determined from each one of a group of Y cardiac signal segments may be compared to each other for determining if monomorphic waveform criteria are satisfied without comparing these signal waveform features to SVT template features.

The template features determined at block 156 may include a polarity pattern, a peak time interval, and an averaged signal width. Example techniques for determining these features are described in conjunction with FIGS. 7 and 8. The template features are stored in memory 82 for use in determining if SVT beat criteria are satisfied when SVT discrimination has been enabled by control circuit 80.

Figure 7:
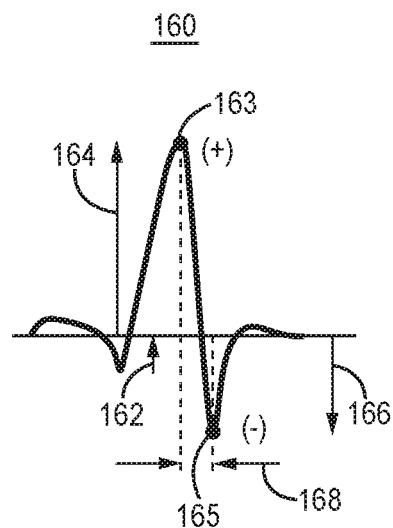
FIG. 7 is a diagram of one example of a cardiac signal segment from which cardiac signal segment features are determined when SVC discrimination is enabled.

FIG. 7 is a diagram of one example of a notch-filtered cardiac signal segment 160 from which cardiac signal segment features are determined at block 108 of FIG. 5 when SVT discrimination is enabled. Cardiac signal segment 160 may include a predetermined number of sample points before and after an R-wave sensed event signal 162 produced by sensing circuit 86, corresponding to the time of a crossing of an R-wave sensing threshold by a cardiac electrical signal. In one example, cardiac signal segment 160 includes 48 sample points with the R-wave sensed event signal 162 occurring at the twenty-fourth sample point.

The R-wave sensed event signal 162 may be produced when cardiac signal segment 160 crosses an R-wave sensing threshold but may be produced when a different cardiac electrical signal, e.g., from a different one of sensing channels 83 and 85, crosses the R-wave sensing threshold. For instance, the first sensing channel 83 may produce R-wave sensed event signal 162 in response to the first cardiac electrical signal received by first sensing channel 83 crossing an R-wave sensing threshold. The cardiac signal segment 160 may be buffered from the second cardiac electrical signal received by control circuit 80 from the second sensing channel 85. The R-wave sensed event signal 162 from the first sensing channel 83 is used as a timing marker for selecting the beginning and ending sample points stored from the second cardiac electrical signal for buffering cardiac signal segment 160. In this way, the first sensing channel 83 may be used for sensing R-waves, and the second sensing channel 85 may be used for acquiring cardiac signal segments from a different sensing vector. Each cardiac signal segment corresponds to an R-wave sensed event signal 162. Cardiac signal segment features are determined from each cardiac signal segment, such as segment 160, for SVT discrimination.

One feature determined from cardiac signal segment 160 may be its polarity pattern. An R-wave signal may have a biphasic polarity having both a pronounced positive and pronounced negative peak. At other times, an R-wave signal may have a monophasic polarity characterized by a single dominant peak, either positive or negative. Control circuit 80 may be configured to identify and discriminate between four polarity patterns: biphasic having a positive peak followed by a negative peak; biphasic having a negative peak followed by a positive peak; monophasic having a positive dominant peak, or monophasic having a negative dominant peak. Polarity pattern values may be assigned to each of the possible polarity patterns for buffering in memory 82 for a predetermined number of cardiac signal segments analyzed during SVT discrimination. For instance, the four polarity patterns listed above may be assigned respective values of 1 through 4. In other examples, polarity patterns identified by control circuit 80 may not be limited to the four patterns listed above; control circuit 80 may be configured to identify fewer, additional or different polarity patterns than the four listed here. Polarity patterns that are identified may be tailored to an individual patient or based on implant locations of sensing electrode vectors. For example, an R-wave signal may include more than two pronounced peaks in a tri-phasic signal or a signal having a pronounced split positive peak and a pronounced negative peak or vice versa.

Control circuit 80 may determine the polarity pattern of cardiac signal segment 160 by determining the maximum positive amplitude 164 of the maximum peak 163 and the maximum negative amplitude 166 of the minimum peak 165. The greatest absolute value of the maximum positive and negative amplitudes 164 and 166, respectively, is identified and may be used by control circuit 80 to set a polarity pattern amplitude threshold. If the absolute values of both of the maximum positive amplitude 164 and maximum negative amplitude 166 are greater than the polarity pattern amplitude threshold, the cardiac signal segment 160 is determined to have a biphasic polarity pattern. If only one of the maximum amplitudes 164 or 166 is greater than the polarity pattern amplitude threshold, the cardiac signal segment is determined to have a monophasic polarity pattern.

In an illustrative example, the polarity pattern amplitude threshold is set to be 25% of the largest one of the maximum positive and negative amplitudes 164 and 166. In the particular example shown in FIG. 7, maximum positive amplitude 164 is greater in absolute value than maximum negative amplitude 166. Control circuit 80 therefore uses the maximum positive amplitude 164 to set the polarity pattern amplitude threshold as 25% of maximum positive amplitude 164. The absolute value of the maximum negative amplitude 166 is compared to the polarity pattern amplitude threshold. Since it is greater than the polarity pattern amplitude threshold, i.e., greater than 25% of the maximum positive amplitude 164 in this example, the cardiac signal segment 160 is determined to have a biphasic polarity pattern.

The control circuit 80 may further determine that the positive peak 163 occurs earlier in time than the negative peak 165 yielding a polarity pattern of biphasic, positive peak first. The sample point numbers of maximum peak 163 and minimum peak 165 may be compared to determine if the biphasic pattern is positive peak first or negative peak first. The sample points in cardiac signal segment 160 may be numbered consecutively from beginning to end, e.g., from 1 to 48 when 48 sample points are included in cardiac signal segment 160. A lower sample point number of maximum peak 163 and a higher sample point number of minimum peak 165 indicate a positive peak first polarity pattern. Control circuit 80 may store a value in memory 82 indicating that the polarity pattern of cardiac signal segment 160 is biphasic, positive peak first.

A second SVT discrimination feature of the cardiac signal segment 160 may be determined as a peak time interval 168. In the example of a biphasic polarity pattern, the peak time interval 168 may be determined as the time interval between the maximum peak 163 and the minimum peak 165. This peak time interval 168 may be determined and stored in memory 82 for cardiac signal segment 160 as the difference between the respective sample point numbers of the maximum positive peak 163 and the minimum negative peak 165.

Figure 8:
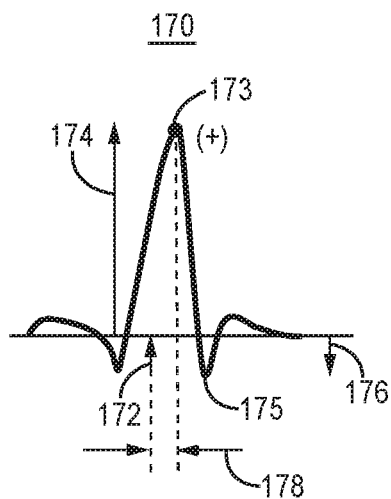
FIG. 8 is a diagram of an example cardiac signal segment having a monophasic polarity pattern.

FIG. 8 is a diagram of an example cardiac signal segment 170 having a monophasic polarity pattern. The maximum positive amplitude 174 is used by control circuit 80 to set the polarity pattern amplitude threshold because it is greater than the maximum negative amplitude 176. The absolute value of the maximum negative amplitude 176 of minimum peak 175 is less than the polarity pattern threshold, which may be set to one-fourth of the maximum positive amplitude 174. The maximum peak 173 is therefore the only dominant peak. Control circuit 80 identifies cardiac signal segment 170 as having a monophasic, positive polarity pattern and stores a polarity pattern value in memory 82 indicating this polarity pattern for cardiac signal segment 170.

When the polarity pattern is determined to be monophasic, the control circuit 80 may determine the peak time interval 178 using a different method than the method used to determine the peak time interval 168 of a biphasic polarity pattern signal 160 as shown in FIG. 7. The peak time interval 178 of a monophasic signal may be determined as the time interval, or sample point number difference, between the R-wave sensed event signal 172 and the dominant peak, maximum peak 173 in this example.

A third SVT discrimination feature that may be determined from cardiac signal segments 160 and 170 of FIGS. 7 and 8, in addition to the peak time interval and the polarity pattern, may be a normalized signal width. The cardiac signal segment 160 or 170 may be rectified and all sample point amplitudes may be summed to obtain an area defined by the signal segment 160 or 170. The area of the signal 160 or 170 may be divided by the largest absolute value of either the maximum peak amplitude 164 or 174 or minimum peak amplitude 166 or 176 of the respective signal segment to obtain the normalized signal width. Each of these three features, namely polarity pattern, peak time interval and normalized signal width, are stored for each buffered cardiac signal segment during SVT discrimination. These three cardiac signal segment features may be used for determining if a sensed R-wave satisfies SVT beat criteria at block 112 of FIG. 5 and as further described in conjunction with FIG. 12 below.

The polarity pattern, peak time interval, and normalized signal width may be determined from the SVT template in a similar manner at block 156 of FIG. 6. In this way, cardiac signal segment features determined from signal segments acquired during an unknown heart rhythm may be compared to analogous SVT template features when SVT discrimination is enabled for determining if SVT beat criteria are satisfied.

Figure 9:
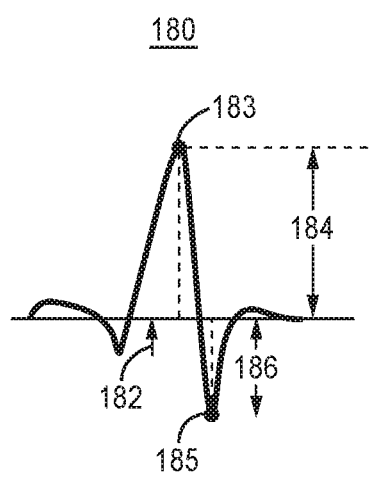
FIG. 9 is a schematic diagram of a method for determining features from a cardiac signal segment for use in determining if monomorphic waveform criteria are satisfied.

FIG. 9 is a schematic diagram of a notch-filtered cardiac signal segment 180 for use in determining if monomorphic waveform criteria are satisfied at block 110 of FIG. 5. In addition to the features determined from cardiac signal segments for determining if SVT beat criteria are satisfied, features are determined from the buffered, cardiac signal segments for applying monomorphic waveform criteria when SVT discrimination is enabled. One feature determined by control circuit 80 for use in confirming whether monomorphic waveform criteria are met may be the maximum peak sample number. As described above, the sample points included in a buffered cardiac signal segment 180 may be numbered consecutively from beginning to end, e.g., from 1 to 48, with the corresponding R-wave sensed event signal 182 at sample point number 24. The polarity of a dominate peak of the SVT template may be determined at block 156 of FIG. 6. The maximum peak sample number of signal segment 180 is determined as the sample point number having a maximum absolute amplitude and the same polarity as the dominate peak of the SVT template.

For example, if the SVT template is identified to have a dominant peak that has a positive polarity, i.e., the absolute maximum amplitude of the SVT template is positive, the sample point number of the maximum peak 183 is identified as the maximum peak sample number. If, however, the SVT template has a maximum absolute amplitude corresponding to a minimum (negative) peak, the sample point number of the minimum peak 185 is determined as the maximum peak sample number. Control circuit 80 may search for a maximum value of all positive values of cardiac signal segment 180 if the dominant peak of the SVT template is positive or search for a minimum of all negative values of the cardiac signal segment 180 if the dominant peak of SVT template is negative. The sample point number of the respective maximum or minimum is stored as the maximum peak sample number for the corresponding cardiac signal segment 180.

In addition to determining the maximum peak sample number, control circuit 80 may determine the maximum peak amplitude 184 or 186 of the maximum peak 183 or 185 that has a polarity matching the dominant peak of the SVT template. In some cases, the maximum peak sample number and maximum peak amplitude determined from cardiac signal segment 180 as SVT discrimination features may or may not correspond to the actual absolute maximum peak amplitude of the segment 180 when the actual absolute maximum peak of segment 180 has a different polarity than the polarity of the greatest absolute amplitude of the SVT template.

A third SVT discrimination feature determined from cardiac signal segment 180 for use in determining if monomorphic waveform criteria are met may be the RRI from the R-wave sensed event signal 182 to the most recent preceding R-wave sensed event signal. The maximum peak sample number and maximum peak amplitude having a polarity matching the polarity of the maximum absolute amplitude of the SVT template and the RRI may all be stored as features of segment 180 for determining if monomorphic waveform criteria are met when SVT discrimination is enabled.

In other examples, the absolute maximum peak of the cardiac signal segment 180 may be identified and its amplitude and sample number may be stored as features of cardiac signal segment 180 regardless of polarity. The maximum peak 183 has a greater amplitude 184 than the amplitude 186 of minimum peak 185. The maximum peak amplitude 184 may be stored as feature of cardiac signal segment 180, along with the sample number of maximum peak 183. If the minimum peak 185 has a larger negative peak amplitude 186 (absolute value) than positive peak amplitude 184, the absolute value of the negative peak amplitude 186 and the sample number of minimum peak 185 may be stored as features of cardiac signal segment 180.

Figure 10:
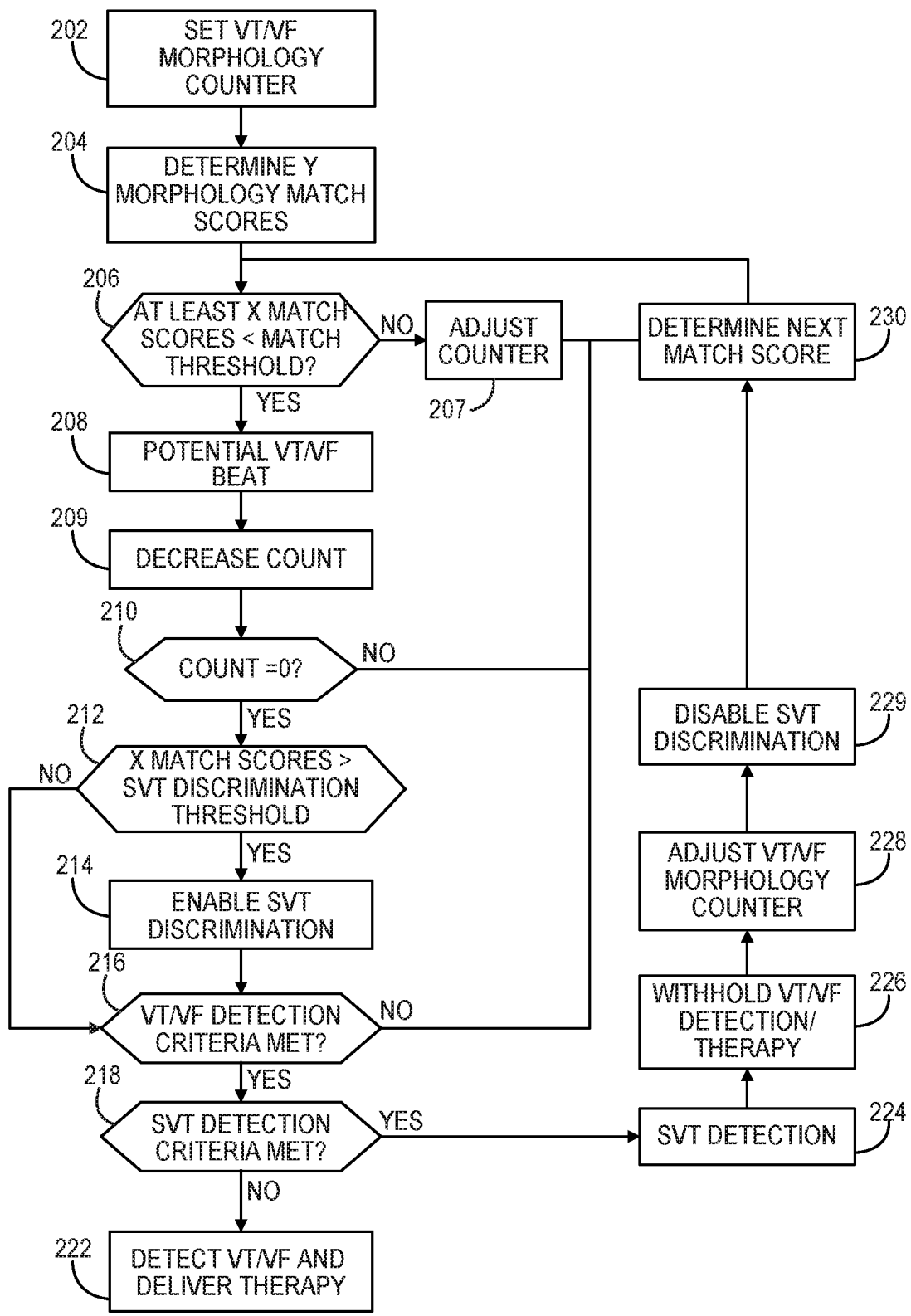
FIG. 10 is a flow chart of a method for discriminating SVT from VT/VF and for adjusting VT/VF morphology criteria according to another example.

FIG. 10 is a flow chart 200 of a method for discriminating SVT from VT/VF and for adjusting VT/VF morphology criteria according to another example. At block 202, control circuit 80 sets a VT/VF morphology count to an initial value. Control circuit 80 may include a counter for counting the number of sensed R-waves classified as a potential VT/VF beat based on at least X of Y most recent cardiac signal segments having a morphology matching score less than a first match threshold. In the illustrative examples presented herein, the counter is initially set to a value of zero so that only a single group of Y cardiac signal segments resulting in the most recent R-wave sensed event signal being classified as a potential VT/VF beat results in VT/VF morphology criteria being met.

At block 204, the morphology match scores for Y cardiac signal segments that are buffered in memory 82 are determined. The Y morphology match scores are compared to the match threshold at block 206. These Y morphology match scores may be compared to the match threshold on a beat-by-beat basis so that each R-wave sensed event signal may be classified as a potential VT/VF beat if at least X of the most recent Y morphology match scores stored in a rolling buffer of memory 82 are less than the first match threshold. If fewer than X of the Y morphology match scores are less than the match threshold, "no" branch of block 206, the most recently sensed R-wave is not classified as a potential VT/VF beat.

In response to not classifying the most recently sensed R-wave as a potential VT/VF beat, control circuit adjusts the VT/VF counter to delay detection of VT or VF. For example, the counter value initialized to zero at block 202 may be set to a non-zero value, e.g., 10, at block 207 when at least X of Y match scores are not less than the match threshold at block 206. This means that more than Y-X morphology match scores are greater than the match threshold and may represent heartbeats that originated in the upper heart chambers, indicating an SVT rhythm. This evidence of an SVT rhythm warrants delaying VT or VF detection. As such, the VT/VF morphology counter value is set to a non-zero value at block 207 to delay a VT/VF detection. For example, each time fewer than X of Y cardiac signal segments have a morphology matching score that is less than the first match threshold, the currently sensed R-wave is not classified as a potential VT/VF beat, and the VT/VF counter is set to 10 at block 207. The VT/VF counter may be required to count down from a non-zero value back to zero before VT or VF can be detected, thereby delaying a VT or VF detection in the presence of morphology-based SVT rhythm evidence. In order to reach a count of zero, 10 consecutively sensed R-waves may be required to be classified as a potential VT/VF beat based on at least X of Y most recent cardiac signal segments having a morphology match score greater than the first match threshold. At block 230, control circuit 80 advances to the next R-wave signal for determining the next morphology match score in a moving window of Y R-wave signals.

Using the previous example, if 6 out of 8 cardiac signal segments have morphology match scores less than a first match threshold of 60, the control circuit 80 classifies the most recently sensed R-wave as a potential VT/VF beat at block 208. The VT/VF morphology counter value is decreased by one at block 209. If the counter value is at zero, e.g., still at an initialized zero value after the evaluation of the first group of Y morphology match scores, no adjustment is needed at block 209. Otherwise, if the counter value had been previously adjusted at block 207, the counter value is decreased by one. If the counter value is not equal to zero at block 210, control circuit 80 advances to block 230 to determine the next morphology match score for the next buffered cardiac signal segment corresponding to the next R-wave sensed event signal. The oldest buffered cardiac signal segment may be dropped, along with its match score, so that a moving window of Y cardiac signal segments is advanced forward by one sensed R-wave. This process of determining the next morphology match score and whether at least X of Y morphology match scores are less than the morphology match threshold (block 206) continues until the VT/VF morphology counter reaches a value of zero at block 210.

If the VT/VF morphology counter value is at zero at block 210, control circuit 80 advances to block 212 to determine if criteria for enabling SVT discrimination are satisfied. A VT/VF morphology counter value of zero indicates that at least one R-wave sensed event signal is classified as a potential VT/VF beat at block 208 based on X of Y match scores being less than the first match threshold. When the VT/VF morphology counter reaches zero the VT/VF morphology criteria may be satisfied, supporting a VT or VF detection if other VT/VF detection criteria are satisfied.

However, postural changes and other factors may influence the cardiac electrical signal received by sensing circuit 86. As a result, relatively low morphology match scores may occur, leading to the VT/VF morphology criteria being satisfied at block 210, at times when the heart rhythm is actually a supraventricular rhythm. As such, before supporting a VT/VF detection based on the VT/VF morphology criteria being satisfied according to a counter value of zero at block 210, control circuit 80 determines if SVT discrimination criteria are met at block 212.

In one example, control circuit 80 enables SVT discrimination at block 214 if at least X of the most recent Y cardiac signal segments have a morphology match score that is greater than a second match threshold at block 212, which may be referred to as an SVT discrimination match threshold. The SVT discrimination match threshold applied at block 212 may be less than the first match threshold applied to morphology match scores at block 206 for determining if VT/VF morphology criteria are satisfied. In the example given above, a first match threshold of 60 is applied at block 206. The SVT match threshold applied at block 212 may bet 20. The SVT discrimination criteria may require that X of Y cardiac signal segments have a morphology match score of at least 20 in order to enable SVT discrimination at block 214.

If this requirement is not met, "no" branch of block 212, control circuit 80 may advance to block 216 to determine if VT/VF detection criteria are met without enabling SVT discrimination. If other VT/VF detection criteria are satisfied, e.g., if a VT or VF interval counter reaches as respective NID, and the VT/VF morphology counter value is at zero as determined at block 210, control circuit 80 may detect VT or VF at block 222, without performing SVT discrimination.

If SVT discrimination criteria are met at block 212, however, control circuit 80 enables SVT discrimination at block 214. Control circuit 80 enables SVT discrimination at block 214 by determining cardiac signal segment features from each buffered cardiac signal segment as described in conjunction with FIGS. 7-9. If VT/VF detection criteria are met at block 216, e.g., if an NID is reached and the VT/VF morphology counter has reached a count of zero at block 210, control circuit 80 determines if SVT detection criteria are met at block 218.

At block 218, a first portion of the features determined from each of the currently buffered cardiac signal segments are used for determining if the group of Y cardiac signal segments represent monomorphic waveforms, and a second portion of the features determined from each of the Y cardiac signal segments are used to determine if the group of Y cardiac signal segments represent SVT beats. Methods for determining whether monomorphic waveform criteria and SVT beat criteria are satisfied are described below in conjunction with FIGS. 11 and 12. If the Y cardiac signal segments are determined to satisfy both monomorphic waveform criteria and SVT beat criteria, SVT detection criteria are satisfied at block 218. SVT is detected at block 224. VT/VF detection is withheld at block 226, and no VT/VF therapy is delivered.

In response to the SVT detection criteria being met at block 218, control circuit 80 may adjust the VT/VF morphology counter to a non-zero value at block 228. In one example, the VT/VF morphology counter, which had reached zero at block 210, may be increased to a value of 5 or another predetermined value, to delay VT/VF detection.

Since the VT/VF morphology counter is no longer at a value of zero, SVT discrimination may be disabled at block 229. The VT/VF morphology counter may be required to count back down to zero from the adjusted count value of 5 before VT or VF can be detected. Control circuit 80 returns to block 230 to advance the moving window of Y R-wave signals to the next sensed R-wave and determines the morphology matching score of the next buffered cardiac signal segment.

If the SVT detection criteria are not met at block 218, and all other VT/VF detection criteria are satisfied, e.g., a VT or VF NID is reached when the VT/VF morphology counter is at a value of zero, VT or VF is detected at block 222. Control circuit 80 may control therapy delivery module 84 to deliver therapy according to programmed therapy protocols for the detected VT or VF episode.

Figure 11:
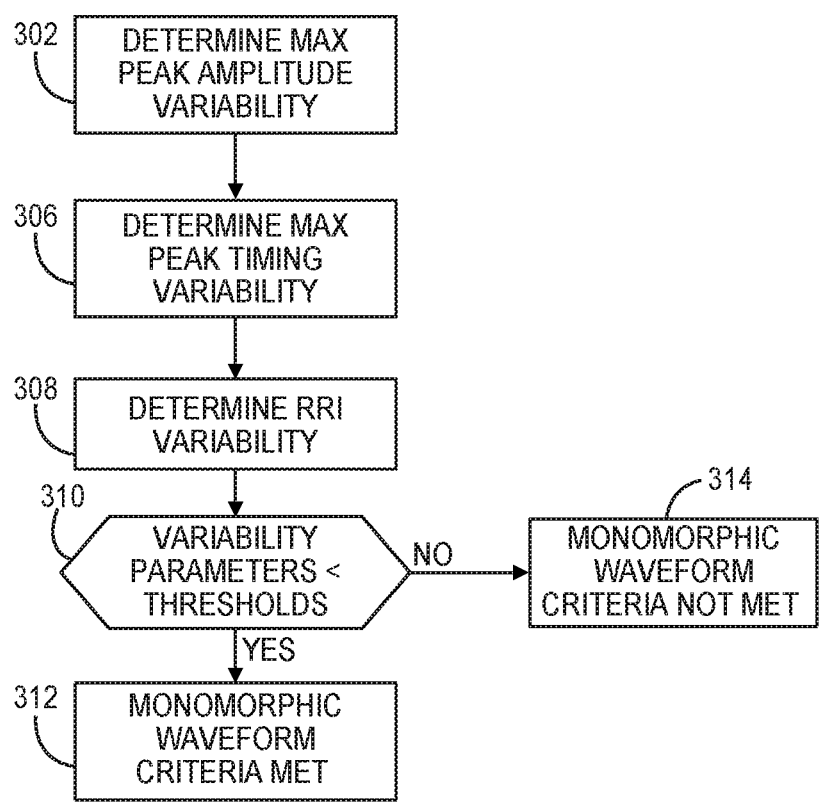
FIG. 11 is a flow chart of a for determining if monomorphic waveform criteria are satisfied according to one example.

FIG. 11 is a flow chart 300 of a method that may be performed at block 110 of FIG. 5 or block 218 of FIG. 10 for determining if monomorphic waveform criteria are satisfied according to one example. After SVT discrimination is enabled at block 106 of FIG. 5 (or block 214 of FIG. 10), control circuit 80 may be configured to determine features from cardiac signal segments buffered in memory 82 corresponding to respective R-wave sensed event signals received from sensing circuit 86. As described above, the cardiac signal segments may be acquired from a second cardiac electrical signal received by second sensing channel 85. The cardiac signal segments may include 48 sample points with the R-wave sensed event signal at sample point 24. The second cardiac electrical signal may be notch filtered by second sensing channel 85 prior to determining the features of the buffered cardiac signal segments.

As described in conjunction with the examples of FIGS. 7-9, six different features are determined from each cardiac signal segment. Those six features include three features determined from each one of the cardiac signal segments for use in determining if monomorphic waveform criteria are met. The other three features determined from each one of the cardiac signal segments are used for determining if SVT beat criteria are met as described below in conjunction with FIG. 12. The features may be determined from each cardiac signal segment on a beat-by-beat basis as each signal segment is acquired and buffered in memory 82. The determined features may be buffered in memory 82 for a predetermined number of signal segments corresponding to consecutively sensed R-waves, e.g., 8 signal segments, in a first-in-first-out basis. In this way, control circuit 80 may determine if SVT is detected using the most recent Y buffered cardiac signal segment features if VT/VF detection criteria become satisfied. The VT/VF detection may be withheld based on an SVT detection.

The three features determined and stored for each one of the cardiac signal segments for determining if monomorphic waveform criteria are met include the maximum peak amplitude, the maximum peak sample number and the RRI as described in conjunction with FIG. 9 above. At block 302, control circuit 80 determines the maximum peak amplitude variability among the Y maximum peak amplitudes determined and stored for the Y cardiac signal segments. The maximum peak amplitude variability may be determined by determining the largest maximum peak amplitude and the smallest maximum peak amplitude among the buffered Y maximum peak amplitudes. The maximum peak amplitude variability may be determined at block 302 as the difference between the largest and smallest maximum peak amplitudes divided by the mean of the Y buffered maximum peak amplitudes.

At block 306 a maximum peak timing variability is determined using the Y maximum peak sample numbers buffered for the Y cardiac signal segments. The maximum peak timing variability may be determined as the difference between the largest and the smallest maximum peak sample numbers stored for the Y cardiac signal segments.

Control circuit 80 determines RRI variability at block 308. RRI variability may be determined by subtracting the smallest RRI from the largest RRI stored for the Y cardiac signal segments and dividing the difference by a mean RRI determined from the Y RRIs. In one example, the mean RRI is a trimmed mean determined by averaging the buffered RRI values after dropping the largest and smallest RRIs. In some examples, the RRI variability may be determined over more than Y cardiac signal segments. For instance, the most recent 12 RRIs may be used for determining RRI variability at block 308. The trimmed mean may be determined by dropping the largest two RRIs and the smallest two RRIs and averaging the remaining 8 RRIs. The difference between the maximum and minimum RRIs of all 12 RRIs may be divided by the trimmed mean to determine the RRI variability at block 308.

It is recognized that other techniques may be used to determine variability in the maximum peak amplitude, the variability in the maximum peak timing, which is related to the timing of the R-wave sensed event signal since the sample point numbering of the signal segment is based on the timing of the R-wave sensed event signal (as shown in FIG. 9), and the variability in RRIs. Once SVT discrimination is enabled, the cardiac signal segment features needed for applying monomorphic waveform criteria may be determined so that the variability of the cardiac signal segment features for the most recent Y cardiac signal segments may be performed on a beat-by-beat basis.

At block 310, control circuit 80 compares each of these variability metrics determined at blocks 302, 306 and 308 to respective thresholds. If each variability metric is less than its respective threshold, indicating relatively low variability in the maximum peak amplitude, maximum peak timing, and RRIs, the monomorphic waveform criteria are satisfied as indicated at block 312. In one example, if the maximum peak amplitude variability is less than 60%, the maximum peak timing variability is less than 8 sample points (for a sampling rate of 256 Hz), and the RRI variability is less than 15%, monomorphic waveform criteria are met. These examples are intended to be illustrative in nature and not limiting; other variability thresholds may be used for identifying monomorphic waveforms.

In some examples, all three variability metrics are required to be less than their respective thresholds, and, if not, the monomorphic waveform criteria are not met as indicated at block 314. In other examples, at least one or two of the variability metrics may be required to be less than their respective threshold in order for monomorphic waveform criteria to be satisfied. In the analysis of FIG. 11, the three features of maximum peak amplitude, maximum peak timing, and RRI determined for each of the buffered Y cardiac signal segments are compared to each other for determining variability metrics and whether or not the corresponding sensed R-waves are monomorphic. These features may not be compared to SVT template features in the example method of FIG. 11 for determining if the Y cardiac signal segments meet monomorphic waveform criteria.

Figure 12:
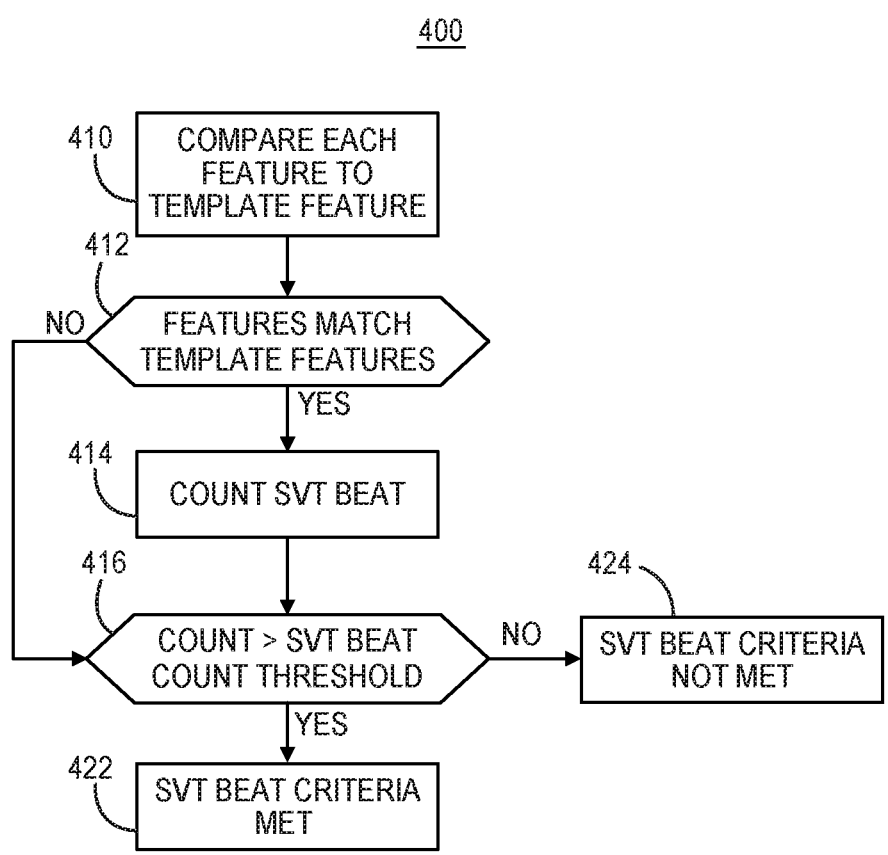
FIG. 12 is a flow chart for determining if SVT beat criteria are satisfied.

FIG. 12 is a flow chart 400 of a method for determining if SVT beat criteria are met at block 112 of FIG. 5 or at block 218 of FIG. 10. In the examples presented in conjunction with FIGS. 7 and 8, the three features determined from buffered cardiac signal segments for determining if SVT beat criteria are met are polarity pattern, peak time interval, and normalized signal width. At block 410, control circuit 80 compares these three features determined from the most recent buffered cardiac signal segment to the analogous three features of the SVT template (determined and stored in memory 82 at block 156 of FIG. 6).

If the three features match the respective SVT template features within a predetermined threshold range, the most recently sensed R-wave corresponding to the cardiac signal segment is counted as an SVT beat at block 414. If the cardiac signal segment features do not match the analogous SVT template features within a predetermined threshold range, the process advances to block 416 without counting the most recently sensed R-wave as an SVT beat.

In one example, the determined polarity pattern of the cardiac signal segment and the SVT template are required to be the same in order to match at block 412. For instance both the cardiac signal segment and the SVT template are biphasic, positive peak first; both are biphasic, negative peak first; both are monophasic, positive peak or both are monophasic, negative peak in order to match. The peak time interval of the cardiac signal segment may be required to within 5 sample points of the peak time interval of the SVT template (for a sampling rate of 256 Hz) in order for the peak time interval to match the SVT template peak time interval. The normalized signal width may be required to be within 30% or another percentage threshold of the SVT template normalized signal width. If each of these three feature comparisons to analogous SVT template features result in a match, the most recently sensed R-wave corresponding to the cardiac signal segment from which the features were derived is counted as an SVT beat at block 414.

Control circuit 80 may include an SVT beat counter for counting each of the most recent Y cardiac signal segments having the three SVT discrimination features matching the SVT template features. If the counter is equal to or greater than an SVT beat count threshold at block 416, the SVT beat criteria are determined to be satisfied at block 422. If the SVT beat counter is not equal to or greater than the SVT beat count threshold at block 416 ("no" branch), the SVT beat criteria for the Y cardiac signal segments are determined to not be met at block 424. The SVT count threshold applied at block 416 may require that 3 out of the most recent 8 cardiac signal segments be counted as SVT beats. In other examples, more or fewer than 3 out of 8 cardiac signal segments may be required to be counted as SVT beats in order to satisfy the SVT beat criteria at block 422.

As described above, if both the monomorphic waveform criteria and the SVT beat criteria are satisfied by the SVT discrimination features determined from the most recent Y cardiac signal segments, SVT detection criteria are met. In other examples, control circuit 80 may require both the monomorphic waveform criteria and the SVT beat criteria be satisfied by the SVT discrimination features determined from the most recent Y cardiac signal segments for more than group of Y cardiac signal segments. For instance, the monomorphic waveform and SVT beat criteria may both be required to be satisfied by the most recent Y cardiac signal segments on three or more consecutively sensed R-waves. If SVT detection criteria are satisfied at the time that VT/VF detection criteria are met, the VT/VF detection is withheld.

Figure 13:
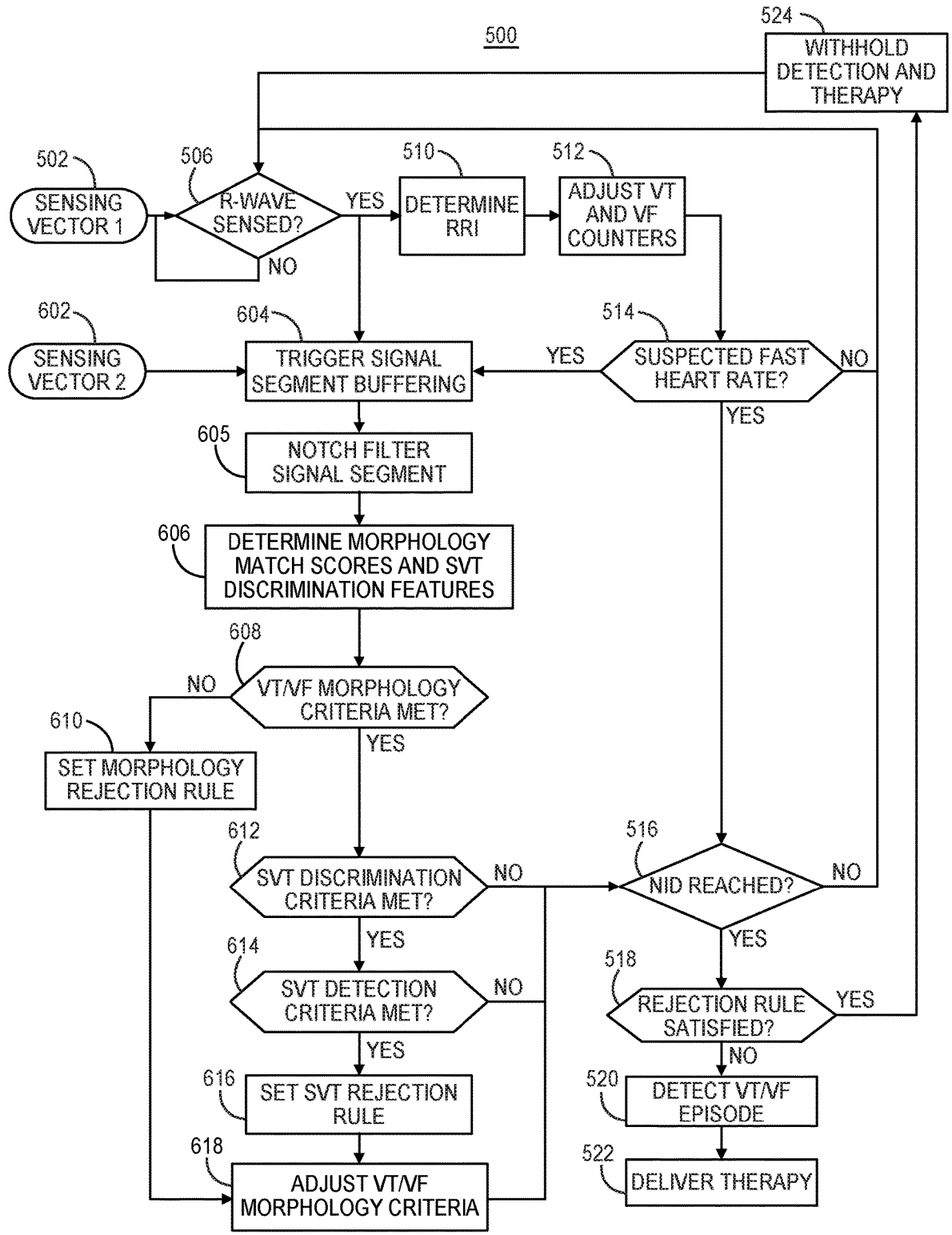
FIG. 13 is a flow chart of a method for detecting ventricular tachyarrhythmias according to one example using the SVT discrimination techniques disclosed herein.

FIG. 13 is a flow chart 500 of a method for detecting ventricular tachyarrhythmias according to one example using the SVT discrimination techniques disclosed herein. At block 502, a sensing electrode vector is selected by sensing circuit 86 for receiving a cardiac electrical signal by first sensing channel 83 used for sensing R-waves. The first sensing vector selected at block 502 for obtaining the cardiac electrical signal used for sensing R-waves may be a relatively short bipole, e.g., between electrodes 28 and 30 or between electrodes 28 and 24 of lead 16 or other electrode combinations as described above. The first sensing vector may be a vertical sensing vector (with respect to an upright or standing position of the patient) or approximately aligned with the cardiac axis for maximizing the amplitude of R-waves in the cardiac electrical signal for reliable R-wave sensing. In other examples, the first sensing vector may be a vector between one electrode carried along the distal portion 25 of lead 16 and the ICD housing 15 (shown in FIG. 1A).

Sensing circuit 86 may produce an R-wave sensed event signal at block 506 in response to the first sensing channel 83 detecting an R-wave sensing threshold crossing by the cardiac electrical signal outside of a blanking period. The R-wave sensed event signal may be passed to control circuit 80. In response to the R-wave sensed event signal, timing circuit 90 of control circuit 80 determines an RRI at block 510 ending with the current R-wave sensed event signal and beginning with the most recent preceding R-wave sensed event signal. The timing circuit 90 of control circuit 80 may pass the RRI timing information to the tachyarrhythmia detection circuit 92 which adjusts tachyarrhythmia interval counters at block 512.

If the RRI is shorter than a tachycardia detection interval (TDI) but longer than a fibrillation detection interval (FDI), i.e., if the RRI is in a tachycardia detection interval zone, a VT interval counter is increased at block 512. If the VT interval counter is configured to count consecutive VT intervals for detecting VT, the VT interval counter may be reset to zero if the RRI is longer than the TDI. If the RRI is shorter than the FDI, the VF counter is increased. The VF counter may be a probabilistic VF counter that counts VF intervals in an X of Y manner such that VF may be detected when a threshold number of VF intervals are detected which are not required to be consecutive. In some examples, a combined VT/VF interval counter is increased if the RRI is less than the TDI.

After updating the tachyarrhythmia interval counters at block 512, tachyarrhythmia detector 92 compares the VT and VF interval counter values to a suspected fast heart rate threshold at block 514, which is less than the respective VT NID and VF NID. If a threshold number of short RRIs are counted, the onset of a fast heart rate is suspected. If a VT or VF detection interval counter has reached fast heart rate threshold, "yes" branch of block 514, control circuit 80 enables cardiac signal segment buffering at block 604. In this example, the determination of morphology match scores between the SVT template and buffered cardiac signal segments may be performed on an event-by-event basis only after at least one of the VT or VF interval counter values has reached fast heart rate threshold. In addition or alternatively to applying a fast heart rate threshold to the individual VT and VF counters, a fast heart rate threshold may be applied to a combined VT/VF interval counter. The fast heart rate threshold may be a value of one or more. Different fast heart rate thresholds may be applied to the VT interval counter and the VF interval counter. For example, the fast heart rate threshold may be a count of two on the VT interval counter and a count of three on the VF interval counter. In other examples, the fast heart rate threshold is a higher number, for example five or higher, but may be less than the number of intervals required to detect VT or VF.

If the fast heart rate threshold is not reached by any of the tachyarrhythmia interval counters at block 514, the control circuit 80 returns to block 506 and waits for the next R-wave sensed event signal. Morphology analysis of cardiac signal segments from the second cardiac electrical signal need not be performed until at least threshold number of VT or VF intervals is counted as an indication of a suspected fast heart rate and in anticipation of an NID being reached. In this way, control circuit 80 may be able to make a determination of whether the VT/VF morphology criteria are satisfied and acquire data for SVT discrimination by the time an NID is reached by either one of the VT or VF interval counters.

If the fast heart rate threshold is reached at block 514, the control circuit 80 enables waveform buffering at block 604. In response to each R-wave sensed event signal produced at block 506 by the first sensing channel 83, control circuit 80 buffers a cardiac electrical signal received by the second sensing channel 85. The sensing circuit 86 selects a second sensing vector at block 602 for receiving the cardiac signal that is buffered for obtaining cardiac signal segments for morphology analysis and SVT discrimination.

A digitized segment of the cardiac electrical signal received by the second sensing channel 85 may be buffered over a time segment defined relative to the sample point time of the R-wave sensing threshold crossing and corresponding R-wave sensed event signal received from sensing circuit 86. The digitized segment may be 100 to 500 ms long, for instance. In one example, the buffered segment of the second cardiac electrical signal is at least 48 sample points obtained at a sampling rate of 256 Hz, or approximately 188 ms, of which 24 sample points may precede and include the sample point at which the R-wave sensed event signal was received and 24 sample points may extend after the sample point at which the R-wave sensed event signal was received. In other examples, the cardiac electrical signal segment may be buffered at block 604 over a longer time interval for use in other cardiac signal analyses performed to detect noise in the cardiac signal, T-wave oversensing, or other sensing issues that may lead to a false VT or VF detection.

The buffered cardiac signal segment may be notch filtered at block 605. The notch filter applied at block 605 may correspond to the filter described in provisional U.S. Patent Application No. 62/367,166, incorporated herein by reference in its entirety. The notch filtering performed at block 605 significantly attenuates 50-60 Hz electrical noise, muscle noise, other EMI, and other noise/artifacts in the stored cardiac signal segment from the second cardiac electrical signal.

In one example, notch filtering performed at block 605 is implemented in firmware as a digital integer filter. The output of the digital notch filter may be determined by firmware implemented in the second sensing channel 85 according to the equation:

$$Y(n)=(x(n)+2x(n-2)+x(n-4))/4$$

where x(n) is the amplitude of the nth sample point of the digital signal received by the notch filter 76 (FIG. 4), x(n−2) is the amplitude of the n−2 sample point, and x(n−4) is the amplitude of the n−4 sample point for a sampling rate of 256 Hz. Y(n) is the amplitude of the nth sample point of the notch-filtered, digital second cardiac electrical signal. At a frequency of 60 Hz, the attenuation of the magnitude of Y(n) is −40 decibels (dB). At a frequency of 50 Hz, the attenuation is −20 dB, and at 23 Hz, which may be typical of an R-wave of the cardiac electrical signal, the attenuation is limited to −3 dB. Notch filtering at block 605 may therefore provide highly attenuated 50 and 60 Hz noise, muscle noise, other EMI, and other electrical noise/artifacts while passing lower frequency cardiac signals in the cardiac electrical signal output of second sensing channel 85.

The sample point numbers indicated in the equation above for determining a notch-filtered signal may be modified as needed when a different sampling rate other than 256 Hz is used, and the resulting frequency response may differ somewhat from the example given above. In other examples, other digital filters may be used for attenuation of 50 and 60 Hz. For example, for a sampling rate of 256 Hz, a filtered signal Y(n) may be determined as Y(n)=(x(n)+x(n−1)+x(n−2)+x(n−3))/4 which may have relatively less attenuation at 50 and 60 Hz but acts as a low-pass, notch filter with relatively greater attenuation at higher frequencies (greater than 60 Hz).

Under the control of control circuit 80, a predetermined number of cardiac signal segments may be stored in memory 82 in a rolling, first-in-first-out buffer. In the illustrative examples described herein, eight cardiac signal segments are buffered in memory 82. At block 606, control circuit 80 may determine morphology match scores for each of the buffered cardiac signal segments on a beat-by-beat basis as each signal segment is stored. The morphology match score may be determined by comparing wavelet transform coefficients determined from a given cardiac signal segment to the wavelet transform coefficients of a previously established SVT template, e.g., as described in conjunction with FIG. 6. Other techniques for determining a morphology match score may be used.

SVT discrimination features may also be derived from each cardiac signal segment that is buffered in memory 82. The six SVT discrimination features described in conjunction with FIGS. 7-9 may be determined for each stored signal segment. As a new cardiac signal segment is stored, the oldest signal segment, along with its morphology match score and SVT discrimination features may be deleted.

At block 608, control circuit 80 determines if VT/VF morphology criteria are met using the buffered morphology match scores determined at block 606. Once the buffer for storing eight cardiac signal segments and corresponding morphology match scores and SVT discrimination features is filled, control circuit 80 determines if at least X out of the Y morphology match scores, e.g., at least 6 out of 8, are less than a first match threshold. If fewer than the threshold number (or percentage) of cardiac signal segments have a morphology match score that is less than the match threshold, the VT/VF morphology criteria are not met. This result indicates that at least Y-X cardiac signal segments have a relatively high correlation to the SVT template and is evidence that the rhythm is supraventricular. If the VT/VF morphology criteria are not met ("no" branch of block 608), a morphology rejection rule may be set at block 610. When requirements for setting this rejection rule are satisfied, a VT or VF detection may be withheld when a VT or VF interval counter reaches a respective NID.

If the VT/VF morphology criteria are met at block 608, control circuit 80 may determine if SVT discrimination criteria are met at block 612. SVT discrimination may be enabled at block 612 when the VT/VF morphology criteria are met and at least X of the Y buffered cardiac signal segments are greater than an SVT discrimination match threshold. For example, if at least 6 out of 8 match scores were less than a first match threshold at block 608, but at least 6 out of 8 match scores are greater than an SVT discrimination match threshold that is less than the first match threshold, SVT discrimination criteria are met and SVT discrimination is enabled at block 612.

Control circuit 80 determines if SVT detection criteria are satisfied at block 614 if SVT discrimination is enabled at block 612. The SVT discrimination features determined from each notch-filtered cardiac signal segment are used to determine if SVT detection criteria are met. A first portion of the features determined for each cardiac signal segment is used to determine if the Y cardiac signal segments are monomorphic waveforms. A second portion of the features determined for each cardiac signal segment is used to determine if SVT beat criteria are met. If the monomorphic waveform criteria are satisfied and the SVT beat criteria are satisfied, SVT detection criteria are satisfied at block 614. The SVT rejection rule is set at block 616. Control circuit 80 may set a rejection rule by setting a bit value stored in a register or memory 82 to a high value, e.g., set to 1, to indicate the rejection rule is satisfied and a VT/VF detection based on NID being met (and/or other detection criteria) should be rejected. If the rejection rule is not set, e.g., a corresponding register bit value being low or zero, a VT/VF detection is not withheld based on the rejection rule.

If the morphology rejection rule is set at block 610, in response to the VT/VF morphology criteria not being met at block 608, or the SVT rejection rule is set at block 616, control circuit 80 may adjust VT/VF morphology criteria at block 618. The VT/VF morphology criteria may be adjusted to increase the time that is required to detect VT or VF because of the evidence of a supraventricular rhythm associated with the morphology rejection rule being set and/or the SVT rejection rule being set. The VT/VF morphology criteria may be adjusted to increase the number of cardiac signal segments required to have a morphology matching score less than the first match threshold before VT or VF can be detected again. For example, a VT/VF morphology counter that counts down to zero as sensed R-waves are classified as potential VT/VF beats may be adjusted to an increased value, e.g., to a value of five or ten as described in conjunction with FIG. 10. In other examples, a VT/VF morphology counter may start at zero and count up as sensed R-waves are classified as potential VT/VF beats. The counter may be reset to zero at block 618 and/or a threshold count value required for satisfying VT/VF morphology criteria may be increased, e.g., from an initial threshold of one to a threshold of five or ten potential VT/VF beats.

If an NID is not reached by one of the VT, VF or combined VT/VF interval counters at block 516, control circuit 80 returns to block 506 to sense the next R-wave, determine the next RRI for updating the interval counters, and buffer the next cardiac signal segment if the. The morphology rejection rule and the SVT rejection rule may be updated on a beat-by-beat basis according to the analysis of the new group of buffered cardiac signal segments.

If the NID is reached at block 516 by one of the VT, VF or combined VT/VF interval counters, control circuit 80 checks at block 518 if a rejection rule has been satisfied. If the morphology rejection rule is set, VT or VF detection is withheld at block 524 even though the NID has been reached. If the SVT rejection rule is set, the VT or VF detection is withheld at block 524, even if the VT/VF morphology criteria have been met at block 608 and the NID is reached at block 516. No therapy is delivered. Control circuit 80 advances to the next sensed R-wave to continue updating the VT and VF interval counters and analyzing the next group of buffered cardiac signal segments to update the status of the morphology and SVT rejection rules.

If the NID is reached and the neither the morphology rejection rule nor the SVT rejection rule are set, meaning that the VT/VF morphology criteria are met and the SVT detection criteria are unmet (or SVT discrimination is not enabled), VT or VF is detected at block 520 according to the interval counter that reached its respective NID. Control circuit 80 controls therapy delivery circuit 84 to deliver a therapy at block 522, which may include ATP, a CV/DF shock, and/or post-shock pacing pulses in some examples.

Figure 14:
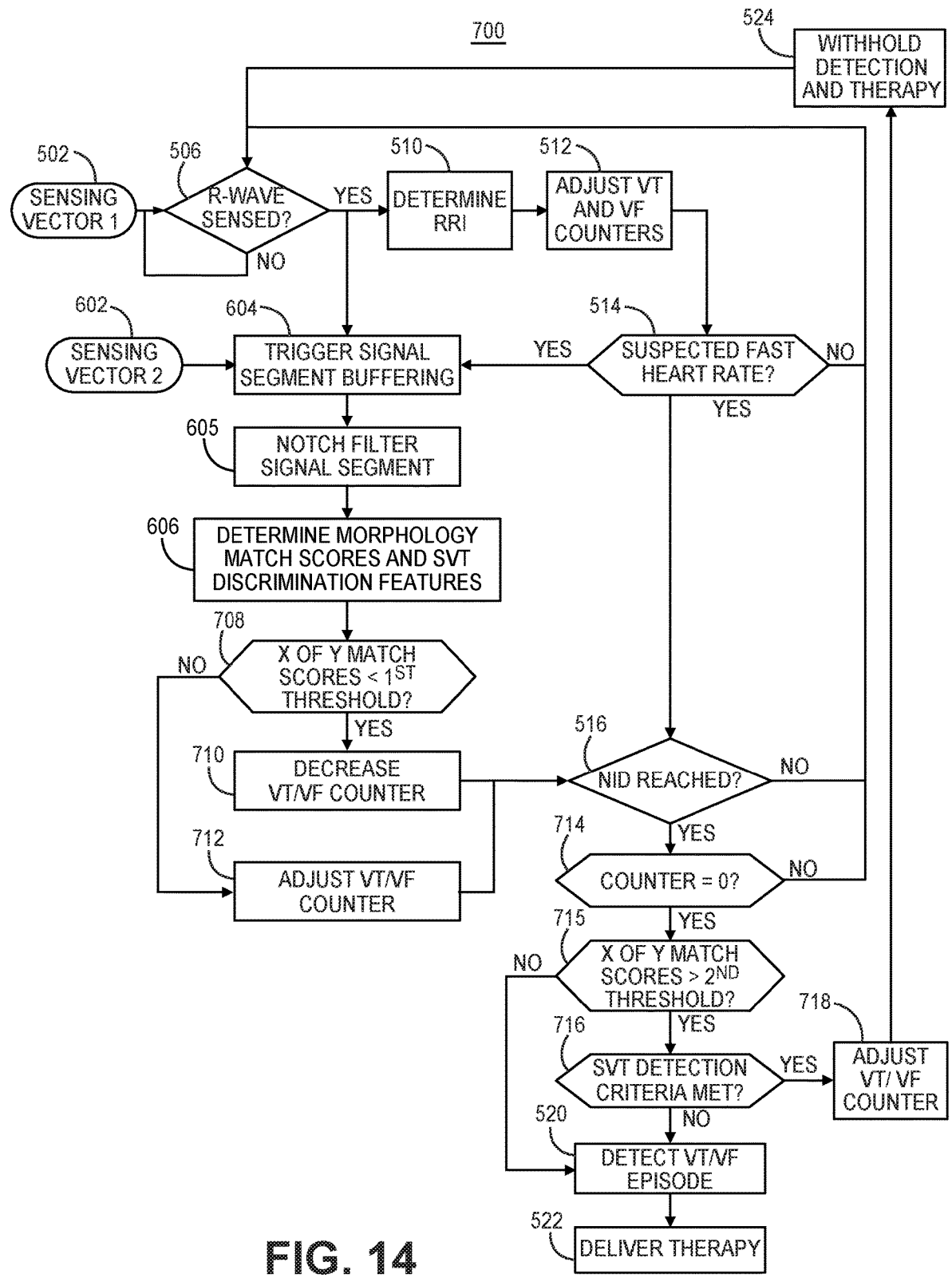
FIG. 14 is a flow chart of a method for detecting ventricular tachyarrhythmias according to another example.

FIG. 14 is a flow chart 700 of a method for detecting ventricular tachyarrhythmias according to another example. Identically-numbered blocks in FIG. 14 correspond to like-numbered blocks described in conjunction with FIG. 13. As described above, VT/VF morphology criteria may be met when X of Y morphology match scores are less than the first match threshold and the VT/VF morphology counter is at a zero value. The VT/VF morphology counter may be initialized to a zero value such that a single sensed R-wave classified as a potential VT/VF beat based on a group of Y morphology match scores satisfies the VT/VF morphology criteria initially.

As shown FIG. 14, after a fast heart rate threshold is reached by a VT or VF interval counter as determined at block 514, cardiac signal segments are stored in memory 82 in a rolling buffer. The morphology match scores and SVT discrimination features of the buffered cardiac signal segments are determined beat-by-beat at block 606. If at least X of Y morphology match scores determined for each buffered cardiac signal segment are less than the first match threshold at block 708, the VT/VF morphology counter is decreased by one at block 710 (unless already at a zero value). If fewer than X of Y morphology match scores are less than the first match threshold, indicating a relatively high correlation between the signal segments and the SVT template, the VT/VF morphology criteria are adjusted by increasing the value of the VT/VF counter at block 712. In one example, each time less than X of Y morphology match scores are less than the first match threshold, the VT/VF morphology counter is set to a value of 10 or another selected value greater than zero.

After either decreasing the VT/VF counter at block 710 or adjusting the VT/VF counter to a non-zero value at block 712, control circuit 80 determines if an NID is reached by any of the VT, VF or combined VT/VF interval counters being updated at block 512. If an NID is reached, control circuit 80 determines if the VT/VF morphology counter is at a value of zero at block 714. If not, VT/VF morphology criteria have not been met and the process returns to block 506 to wait for the next R-wave sensed event signal.

If the VT/VF morphology counter is at a value of zero at block 714, control circuit 80 determines if SVT discrimination criteria are met by determining if at least X of Y match scores stored in memory 82 for the buffered cardiac signal segments are greater than the second match threshold, which is lower than the first match threshold, at block 715. If not, the Y cardiac signal segments have very low correlation to the SVT template. No SVT discrimination is needed. The VT/VF detection criteria are satisfied based on an NID being reached at block 516 and the VT/VF morphology criteria being satisfied at block 714. VT or VF is detected at block 520.

If at least X of Y morphology match scores are greater than the second, SVT discrimination threshold at block 715, control circuit 80 determines if SVT detection criteria are met at block 716. As described previously, e.g., in conjunction with FIGS. 11 and 12, SVT discrimination features determined from the buffered cardiac signal segments at block 606 are analyzed to determine if monomorphic waveform criteria are met and if SVT beat criteria are met. If at least one of the monomorphic waveform criteria or the SVT beat criteria are not satisfied, the SVT detection criteria are not met at block 716 ("no" branch). VT or VF is detected at block 520, and an appropriate therapy is delivered at block 522. In other examples, SVT detection criteria are met when one of the monomorphic waveform criteria or the SVT beat criteria are met so that SVT detection criteria are not met at block 716 only when both of the monomorphic waveform criteria and the SVT beat criteria are not met.

If SVT detection criteria are met at block 716, e.g., both the monomorphic waveform criteria and the SVT beat criteria are satisfied, the VT/VF morphology criteria are adjusted at block 718 by setting the VT/VF morphology counter to a non-zero value, e.g., to a value of five. VT/VF detection is effectively withheld and delayed by requiring the VT/VF morphology counter to count back down to a value of zero before VT or VF can be detected. In order to return to a value of zero in the illustrative examples presented herein, the VT/VF morphology counter must be decreased by one at block 710 on five consecutively sensed R-waves based on X of Y most recent morphology match scores being less than the first match threshold on each of the five consecutively sensed R-waves. If SVT detection criteria are met at block 716, VT/VF detection is withheld at block 524 after adjusting the VT/VF counter, and no therapy is delivered even though both the NID was reached at block 516 and the VT/VF morphology criteria were met based on a VT/VF morphology counter value of zero at block 714.

Thus, techniques for withholding a VT or VF detection based on cardiac signal segment features satisfying SVT detection criteria, even when both RRI-based and waveform morphology-based VT/VF detection criteria are satisfied, are presented herein. The cardiac signal segment feature analysis for SVT discrimination avoids false VT or VF detections in the situation of an altered cardiac signal morphology due to positional changes of the patient's body or posture or other factors that may influence the cardiac signal waveforms such as R-waves (or QRS complexes). The techniques disclosed herein may be implemented in conjunction with additional VT/VF rejection rules that cause a VT or VF detection to be withheld based on additional analysis of the buffered cardiac signal segments. Various cardiac signal analysis techniques and VT/VF rejection rules that may be implemented in conjunction with the SVT discrimination techniques disclosed herein are generally disclosed in provisionally filed U.S. Patent Application No. 62/367,166 , U.S. Patent Application No. 62/367,170 , U.S. Patent Application No. 62/367,221 and U.S. patent application Ser. No. 15/140,802 (Zhang, et al.), all of which are incorporated herein by reference in their entirety. Additional analysis may be performed for detecting electromagnetic interference or other noise in the cardiac electrical signal, T-wave oversensing or verifying sensed R-waves. These additional analyses may be used for other rejection rules for withholding a VT or VF detection when an NID is reached. As such, control circuit 80 may check the status of multiple rejection rules at block 518 of FIG. 13, as generally disclosed in the above-incorporated patent applications.

Thus, an ICD system and method for discriminating SVT from ventricular tachyarrhythmias and withholding a ventricular tachyarrhythmia detection and therapy in response to detecting SVT have been presented in the foregoing description with reference to specific embodiments. In other examples, various methods described herein may include steps performed in a different order or different combination than the illustrative examples shown and described herein. It is appreciated that various modifications to the referenced embodiments may be made without departing from the scope of the disclosure and the following claims.

The invention claimed is:

1. An implantable cardioverter defibrillator (ICD) comprising:
 a therapy delivery circuit configured to generate an electrical stimulation therapy for delivery to a patient's heart;
 a sensing circuit configured to receive at least a first cardiac electrical signal via a sensing electrode vector; and
 a control circuit coupled to the sensing circuit and the therapy delivery circuit and configured to:
  determine whether first criteria for detecting a ventricular tachyarrhythmia are met by the first cardiac electrical signal;
  determine a plurality of features from each one of a plurality of cardiac signal segments of the first cardiac electrical signal;
  in response to the first criteria being met, determine whether a first portion of the plurality of features determined from each one of the plurality of cardiac signal segments satisfy monomorphic waveform criteria;
  determine whether a second portion of the plurality of features determined from each one of the plurality of cardiac signal segments satisfy supraventricular beat criteria by comparing each feature of the second portion of the features determined from each of the plurality of cardiac signal segments to an analogous feature of a supraventricular R-wave template and determining that the supraventricular beat criteria are satisfied in response to a threshold number of the cardiac signal segments having the second portion of the features matching the analogous features of the supraventricular R-wave template;
  determine whether second criteria for detecting the ventricular tachyarrhythmia are met;
  withhold detecting of the ventricular tachyarrhythmia in response to both the monomorphic waveform criteria and the supraventricular beat criteria being satisfied; and
  detect the ventricular tachyarrhythmia and controlling the therapy delivery circuit to deliver the electrical stimulation therapy in response to the first criteria and the second criteria being met and at least one of the monomorphic waveform criteria not being satisfied or the supraventricular beat criteria not being satisfied.

2. The system of claim 1, wherein the control circuit is configured to determine whether the first criteria are met by:
 determining a morphology match score between each one of a plurality of cardiac signal segments of the first cardiac signal and a morphology template;
 determining that the first criteria are met in response to a first threshold number of the plurality of cardiac signal segments having a morphology match score less than a first match threshold.

3. The system of claim 2, wherein the control circuit is further configured to:
 in response to the first criteria being met, determine whether supraventricular tachyarrhythmia discrimination criteria are met;
 withhold determining the plurality of features in response to the supraventricular tachyarrhythmia discrimination criteria not being met; and
 detect the ventricular tachyarrhythmia in response to the first and second criteria for detecting the ventricular tachyarrhythmia being met and the supraventricular tachyarrhythmia discrimination criteria not being met.

4. The system of claim 3, wherein the control circuit is configured:
to determine that the supraventricular tachyarrhythmia discrimination criteria are met by determining that at least a second threshold number of the plurality of cardiac signal segments have a morphology match score greater than a second match threshold, the second match threshold less than the first match threshold.

5. The system of claim 2, wherein the control circuit is further configured to:
set a threshold count value in response to less than the threshold number of the plurality of cardiac signal segments having a morphology match score less than the first match threshold;
adjust a tachyarrhythmia count value in response to the threshold number of a next plurality of cardiac signal segments having morphology match scores less than the first match threshold; and
determine that the first criteria are met when the tachyarrhythmia count value reaches the threshold count value.

6. The system of claim 1, wherein the control circuit is further configured to:
determine sensed event intervals between consecutive R-waves sensed by the sensing circuit;
compare the sensed event intervals to a tachyarrhythmia detection interval;
increase a count of tachyarrhythmia detection intervals in response to each one of the determined sensed event intervals that is less than the tachyarrhythmia detection interval; and
in response to a value of the count of tachyarrhythmia detection intervals being equal to or greater than a fast heart rate threshold, determine whether the first criteria for detecting the ventricular tachyarrhythmia are met.

7. The system of claim 1, wherein the control circuit is configured to:
determine the features for each one of the plurality of cardiac signal segments by determining at least a polarity pattern, a peak time interval; and a normalized width for each one of the plurality of cardiac signal segments; and
determine whether the supraventricular beat criteria are satisfied by:
determining, for each of the plurality of cardiac signal segments, whether the determined polarity pattern matches a polarity pattern of a supraventricular R-wave template;
determining, for each of the plurality of cardiac signal segments, whether the determined peak time interval matches a peak time interval of the supraventricular R-wave template within a peak time interval match threshold range;
determining, for each one of the plurality of cardiac signal segments, whether the determined normalized width matches a normalized width of the supraventricular R-wave within a normalized width match threshold range; and
determining that the supraventricular beat criteria are satisfied in response to a threshold number of the cardiac signal segments having the determined features of polarity pattern, maximum peak amplitude and normalized width matching the analogous features of the supraventricular R-wave template.

8. The system of claim 1, wherein the control circuit is configured to determine whether the monomorphic waveform criteria are satisfied by:
determining a variability of each of the features of the first portion of the features determined from each of the plurality of cardiac signal segments;
comparing the variability of each of the features of the first portion of the features to a respective variability threshold;
determining that the monomorphic waveform criteria are satisfied in response to the variability of each of the features of the first portion of the features being less than the respective variability threshold.

9. The system of claim 1, wherein the control circuit is configured to:
determine a polarity of a maximum peak of a supraventricular R-wave template;
determine the features for each one of the plurality of cardiac signal segments by determining at least an amplitude and timing of a maximum peak of the cardiac signal segment that has a polarity matching the polarity of the maximum peak of the supraventricular R-wave template;
determine an amplitude variability and a timing variability of the maximum peaks of the plurality of cardiac signal segments; and
determine that the monomorphic waveform criteria are satisfied in response to the amplitude variability being less than an amplitude variability threshold and the timing variability being less than a timing variability threshold.

10. The system of claim 1, wherein the control circuit is further configured to:
determine event intervals between consecutive events sensed by the sensing circuit;
compare the event intervals to a tachyarrhythmia detection interval;
increase a count of tachyarrhythmia detection intervals in response to each one of the determined event intervals that is less than the tachyarrhythmia detection interval;
determine that the second criteria for detecting the ventricular tachyarrhythmia are met in response to a value of the count of tachyarrhythmia detection intervals being equal to or greater than a detection threshold value.

11. The system of claim 1, wherein:
the sensing circuit comprises a first sensing channel for receiving the first cardiac signal and a second sensing channel for receiving a second cardiac signal and configured to sense R-waves from the second cardiac signal and produce an R-wave sensed event signal in response to each sensed R-wave;
the control circuit is configured to:
determine a sensed event interval between each consecutive pair of R-wave sensed event signals produced by the sensing circuit;
compare the sensed event intervals to a tachyarrhythmia detection interval;
increase a count of tachyarrhythmia detection intervals in response to each one of the determined sensed event intervals that is less than the tachyarrhythmia detection interval;
buffer the plurality of cardiac signal segments from the first cardiac signal in response to a value of the count of tachyarrhythmia detection intervals being equal to or greater than a fast heart rate threshold, each one of the plurality of cardiac signal segments corresponding to an R-wave sensed event signal produced by the sensing circuit; and determine that the second criteria for detecting the ventricular tachyarrhythmia are met in response to the count of the tachyarrhythmia detection intervals being equal to or greater than a detection threshold value.

12. The system of claim 1, wherein the control circuit is further configured to adjust the first criteria in response to both of the monomorphic waveform criteria and the supraventricular beat criteria being satisfied.

13. An implantable cardioverter defibrillator, comprising:
a therapy delivery circuit configured to generate an electrical stimulation therapy for delivery to a patient's heart;
a sensing circuit configured to receive at least a first cardiac electrical signal via a sensing electrode vector;
a control circuit coupled to the sensing circuit and the therapy delivery circuit and configured to:
    determine whether first criteria for detecting a ventricular tachyarrhythmia are met by the first cardiac electrical signal;
    determine a plurality of features from each one of a plurality of cardiac signal segments of the first cardiac electrical signal;
    in response to the first criteria being met, determine whether a first portion of the plurality of features determined from each one of the plurality of cardiac signal segments satisfy monomorphic waveform criteria;
    determine whether a second portion of the plurality of features determined from each one of the plurality of cardiac signal segments satisfy supraventricular beat criteria by comparing each feature of the second portion of the features determined from each of the plurality of cardiac signal segments to an analogous feature of a supraventricular R-wave template and determining that the supraventricular beat criteria are satisfied in response to a threshold number of the cardiac signal segments having the second portion of the features matching the analogous features of the supraventricular R-wave template;
    determine whether second criteria for detecting the ventricular tachyarrhythmia are met;
    withhold detecting of the ventricular tachyarrhythmia in response to both the monomorphic waveform criteria and the supraventricular beat criteria being satisfied; and
    detect the ventricular tachyarrhythmia and controlling the therapy delivery circuit to deliver the electrical stimulation therapy in response to the first criteria and the second criteria being met and at least one of the monomorphic waveform criteria not being satisfied or the supraventricular beat criteria not being satisfied; and
a housing enclosing the therapy delivery circuit, the sensing circuit and the control circuit, the housing having a connector block for receiving an extra-cardiovascular lead carrying at least one electrode of the sensing electrode vector.

14. A method comprising:
receiving by a sensing circuit at least a first cardiac electrical signal via a sensing electrode vector;
determining by a control circuit whether first criteria for detecting a ventricular tachyarrhythmia are met by the first cardiac electrical signal;
determining a plurality of features for each one of a plurality of cardiac signal segments of the first cardiac electrical signal;
in response to the first criteria being met, determining whether a first portion of the plurality of features determined from each one of the plurality of cardiac signal segments satisfy monomorphic waveform criteria;
determining whether a second portion of the plurality of features determined from each one of the plurality of cardiac signal segments satisfy supraventricular beat criteria by comparing each feature of the second portion of the features determined from each of the plurality of cardiac signal segments to an analogous feature of a supraventricular R-wave template and determining that the supraventricular beat criteria are satisfied in response to a threshold number of the cardiac signal segments having the second portion of the features matching the analogous features of the supraventricular R-wave template;
determining whether second criteria for detecting the ventricular tachyarrhythmia are met;
determining whether both the first portion of the plurality of features satisfy the monomorphic waveform criteria and the second portion of the plurality of features satisfy the supraventricular beat criteria;
withholding detecting of the ventricular tachyarrhythmia in response both the first portion of the plurality of features satisfying the monomorphic waveform criteria and the second portion of the plurality of features satisfying the supraventricular beat criteria; and
detecting the ventricular tachyarrhythmia and controlling the therapy delivery circuit to deliver the electrical stimulation therapy in response to the first criteria and the second criteria being met and at least one of the first portion of the plurality of features not satisfying the monomorphic waveform criteria and/or the second portion of the plurality of features not satisfying the supraventricular beat criteria.

15. The method of claim 14, wherein determining whether the first criteria are met comprises:
determining a morphology match score between each one of a plurality of cardiac signal segments of the first cardiac signal and a morphology template;
determining that the first criteria are met in response to a first threshold number of the plurality of cardiac signal segments having a morphology match score less than a first match threshold.

16. The method of claim 15, further comprising:
in response to the first criteria being met, determining whether supraventricular tachyarrhythmia discrimination criteria are met;
withholding determining the plurality of features in response to the supraventricular tachyarrhythmia discrimination criteria not being met; and
detecting the ventricular tachyarrhythmia in response to the first and second criteria for detecting the ventricular tachyarrhythmia being met and the supraventricular tachyarrhythmia discrimination criteria not being met.

17. The method of claim 16, further comprising:
determining that the supraventricular tachyarrhythmia discrimination criteria are met by determining that at least a second threshold number of the plurality of cardiac signal segments have a morphology match score greater than a second match threshold, the second match threshold less than the first match threshold.

18. The method of claim 15, further comprising:
setting a threshold count value in response to less than the threshold number of the plurality of cardiac signal segments having a morphology match score less than the first match threshold;
adjusting a tachyarrhythmia count value in response to the threshold number of a next plurality of cardiac signal segments having morphology match scores less than the first match threshold; and
determining that the first criteria are met when the tachyarrhythmia count value reaches the threshold count value.

19. The method of claim 14, further comprising:
determining sensed event intervals between consecutive R-waves sensed by the sensing circuit;
comparing the sensed event intervals to a tachyarrhythmia detection interval;
increasing a count of tachyarrhythmia detection intervals in response to each one of the determined sensed event intervals that is less than the tachyarrhythmia detection interval; and
in response to a value of the count of tachyarrhythmia detection intervals being equal to or greater than a fast heart rate threshold, determining whether the first criteria for detecting the ventricular tachyarrhythmia are met.

20. The method of claim 14, wherein:
determining the features for each one of the plurality of cardiac signal segments comprises determining at least a polarity pattern, a peak time interval; and a normalized width for each one of the plurality of cardiac signal segments; and
determining whether the supraventricular beat criteria are satisfied comprises:
determining, for each of the plurality of cardiac signal segments, whether the determined polarity pattern matches a polarity pattern of a supraventricular R-wave template;
determining, for each of the plurality of cardiac signal segments, whether the determined peak time interval matches a peak time interval of the supraventricular R-wave template within a peak time interval match threshold range;
determining, for each one of the plurality of cardiac signal segments, whether the determined normalized width matches a normalized width of the supraventricular R-wave within a normalized width match threshold range; and
determining whether a threshold number of the cardiac signal segments have the determined features of polarity pattern, maximum peak amplitude and normalized width matching the analogous features of the supraventricular R-wave template.

21. The method of claim 14, wherein determining whether the monomorphic waveform criteria are satisfied comprises:
determining a variability of each of the features of the first portion of the plurality of features determined from each of the plurality of cardiac signal segments;
comparing the variability of each of the features of the first portion to a respective variability threshold; and
determining that the monomorphic waveform criteria are satisfied in response to the variability of each of the features of the first portion of the plurality of features being less than the respective variability threshold.

22. The method of claim 14, further comprising:
determining a polarity of a maximum peak of a supraventricular R-wave template;
determining the features for each one of the plurality of cardiac signal segments by determining at least an amplitude and timing of a maximum peak of the cardiac signal segment that has a polarity matching the polarity of the maximum peak of the supraventricular R-wave template;
determining an amplitude variability and a timing variability of the maximum peaks of the plurality of cardiac signal segments; and
determining that the monomorphic waveform criteria are satisfied in response to the amplitude variability being less than an amplitude variability threshold and the timing variability being less than a timing variability threshold.

23. The method of claim 14, further comprising:
determining event intervals between consecutive events sensed by the sensing circuit;
comparing the event intervals to a tachyarrhythmia detection interval;
increasing a count of tachyarrhythmia detection intervals in response to each one of the determined event intervals that is less than the tachyarrhythmia detection interval;
determining that the second criteria for detecting the ventricular tachyarrhythmia are met in response to a value of the count of tachyarrhythmia detection intervals being equal to or greater than a detection threshold value.

24. The method of claim 14, further comprising:
receiving the first cardiac signal by a first sensing channel of the sensing circuit;
receiving a second cardiac signal by a second sensing channel of the sensing circuit;
sensing R-waves from the second cardiac signal;
producing an R-wave sensed event signal in response to each sensed R-wave, determining a sensed event interval between each consecutive pair of the R-wave sensed event signals produced by the sensing circuit;
comparing the sensed event intervals to a tachyarrhythmia detection interval;
increasing a count of tachyarrhythmia detection intervals in response to each one of the determined sensed event intervals that is less than the tachyarrhythmia detection interval;
buffering the plurality of cardiac signal segments from the first cardiac signal in response to a value of the count of tachyarrhythmia detection intervals being equal to or greater than a sensed event confirmation threshold, each one of the plurality of cardiac signal segments corresponding to an R-wave sensed event signal produced by the sensing circuit; and
determining that the second criteria for detecting the ventricular tachyarrhythmia are met in response to the count of the tachyarrhythmia detection intervals being equal to or greater than a detection threshold value.

25. The method of claim 14, further comprising adjusting the first criteria in response to both of the monomorphic waveform criteria and the supraventricular beat criteria being satisfied.

26. The method of claim 14, further comprising receiving the first cardiac electrical signal via the sensing electrode vector comprising at least one electrode carried by an extra-cardiovascular lead.

27. A non-transitory, computer-readable storage medium comprising a set of instructions which, when executed by a control circuit of an implantable cardioverter defibrillator (ICD), cause the ICD to:

receive by a sensing circuit a cardiac electrical signal via a sensing electrode vector;

determine whether first criteria for detecting a ventricular tachyarrhythmia are met by the cardiac electrical signal;

determine a plurality of features for each one of a plurality of cardiac signal segments of the cardiac electrical signal;

in response to the first criteria being met, determine whether a first portion of the plurality of features determined from each one of the plurality of cardiac signal segments satisfy monomorphic waveform criteria;

determine whether a second portion of the plurality of features determined from each one of the plurality of cardiac signal segments satisfy supraventricular beat criteria by comparing each feature of the second portion of the features determined from each of the plurality of cardiac signal segments to an analogous feature of a supraventricular R-wave template and determining that the supraventricular beat criteria are satisfied in response to a threshold number of the cardiac signal segments having the second portion of the features matching the analogous features of the supraventricular R-wave template;

determine whether second criteria for detecting the ventricular tachyarrhythmia are met;

withhold detecting of the ventricular tachyarrhythmia in response to both the monomorphic waveform criteria being satisfied and the supraventricular beat criteria being satisfied; and detect the ventricular tachyarrhythmia and deliver an electrical stimulation therapy by a therapy delivery circuit in response to the first criteria and the second criteria being met and at least one of the monomorphic waveform criteria not being satisfied or the supraventricular beat criteria not being satisfied.

* * * * *